United States Patent
Harris et al.

(10) Patent No.: US 8,992,779 B2
(45) Date of Patent: Mar. 31, 2015

(54) SYSTEM AND PROCESS FOR RECOVERING PRODUCTS USING SIMULATED-MOVING-BED ADSORPTION

(71) Applicant: UOP LLC, Des Plaines, IL (US)

(72) Inventors: James W. Harris, Palatine, IL (US); Jason T. Corradi, Arlington Heights, IL (US); Lewis H. Pettengill, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 298 days.

(21) Appl. No.: 13/630,698

(22) Filed: Sep. 28, 2012

(65) Prior Publication Data
US 2013/0153504 A1    Jun. 20, 2013

Related U.S. Application Data

(60) Provisional application No. 61/570,936, filed on Dec. 15, 2011.

(51) Int. Cl.
| | | |
|---|---|---|
| *C07C 7/17* | (2006.01) | |
| *B01D 15/00* | (2006.01) | |
| *B01D 15/18* | (2006.01) | |
| *C07C 7/13* | (2006.01) | |
| *C07C 15/08* | (2006.01) | |

(52) U.S. Cl.
CPC .............. *B01D 15/1835* (2013.01); *C07C 7/13* (2013.01); *C07C 15/08* (2013.01)
USPC ........... 210/660; 210/672; 210/676; 210/677; 210/690; 585/826

(58) Field of Classification Search
USPC ........... 210/660, 672, 676, 677, 690; 585/826
See application file for complete search history.

(56) References Cited

U.S. PATENT DOCUMENTS

| | | | |
|---|---|---|---|
| 3,201,491 A | 8/1965 | Stine | |
| 3,455,815 A | 7/1969 | Fickel | |
| 3,715,409 A | 2/1973 | Broughton | |
| 3,732,325 A | 5/1973 | Pharis | |
| 3,761,533 A | 9/1973 | Otani | |
| 4,031,156 A | 6/1977 | Geissler | |
| 5,750,820 A | 5/1998 | Wei | |
| 5,884,777 A * | 3/1999 | Pan et al. ................ | 210/672 |
| 5,912,395 A | 6/1999 | Noe | |
| 6,004,518 A | 12/1999 | Green | |
| 6,149,874 A | 11/2000 | Hotier | |
| 7,208,651 B2 * | 4/2007 | Frey .......................... | 585/828 |

OTHER PUBLICATIONS

U.S. Appl. No. 13/630,649, filed Sep. 28, 2012, Jason T. Corradi, Sep. 17, 2004.
U.S. Appl. No. 13/630,608, filed Sep. 28, 2012, Jason T. Corradi.
U.S. Appl. No. 13/630,447, filed Sep. 28, 2012, James W. Harris.
U.S. Appl. No. 13/630,461, filed Sep. 28, 2012, Jason T. Corradi.
U.S. Appl. No. 13/630,415, filed Sep. 28, 2012, Stanley J. Frey, Sep. 17, 2004.
U.S. Appl. No. 13/630,428, filed Sep. 28, 2012, Stanley J. Frey.

* cited by examiner

*Primary Examiner* — Chester Barry

(57) ABSTRACT

A process according to various approach includes flushing an intermediate transfer line between the first intermediate transfer line and the extract stream transfer line away from the adsorptive separation chamber to remove residual fluid from intermediate transfer line. The process may include directing the residual fluid flushed from the intermediate transfer line to a recycle stream to introduce the residual fluid into the adsorptive separation chamber.

18 Claims, 11 Drawing Sheets

SYSTEM AND PROCESS FOR RECOVERING PRODUCTS USING SIMULATED-MOVING-BED ADSORPTION

CROSS-REFERENCE TO RELATED APPLICATION

This application claims benefit of U.S. Provisional Application No. 61/570,936 which was filed on Dec. 15, 2011.

FIELD OF THE INVENTION

The subject invention relates to a process for the adsorptive separation of a preferentially adsorbed component from a feed stream. More specifically, the invention relates to a process for the continuous simulated countercurrent adsorptive separation of aromatic hydrocarbons.

BACKGROUND OF THE INVENTION

Para-xylene and meta-xylene are important raw materials in the chemical and fiber industries. Terephthalic acid derived from para-xylene is used to produce polyester fabrics and other articles which are in wide use today. Meta-xylene is a raw material for the manufacture of a number of useful products including insecticides and isophthalic acid. One or a combination of adsorptive separation, crystallization and fractional distillation have been used to obtain these xylene isomers, with adsorptive separation capturing a great majority of the market share of newly constructed plants for the dominant para-xylene isomer.

Processes for adsorptive separation are widely described in the literature. For example, a general description directed to the recovery of para-xylene was presented at page 70 of the September 1970 edition of CHEMICAL ENGINEERING PROGRESS (Vol. 66, No 9). There is a long history of available references describing useful adsorbents and desorbents, mechanical parts of a simulated moving-bed system including rotary valves for distributing liquid flows, the internals of the adsorbent chambers and control systems. The principle of using a simulated moving bed to continuously separate the components of a fluid mixture by contact with a solid adsorbent is as set forth in U.S. Pat. No. 2,985,589. U.S. Pat. No. 3,997,620 applies the principle of the simulated moving bed to the recovery of para-xylene from a feed stream containing $C_8$ aromatics, and U.S. Pat. No. 4,326,092 teaches meta-xylene recovery from a $C_8$-aromatics stream.

Adsorptive separation units processing $C_8$ aromatics generally use a simulated countercurrent movement of the adsorbent and the feed stream. This simulation is performed using established commercial technology wherein the adsorbent is held in place in one or more cylindrical adsorbent chambers and the positions at which the streams involved in the process enter and leave the chambers are slowly shifted along the length of the beds. A typical adsorptive separation unit is illustrated in FIG. 8 and includes at least four streams (feed, desorbent, extract and raffinate) employed in this procedure and the location at which the feed and desorbent streams enter the chamber and the extract and raffinate streams leave the chamber are simultaneously shifted in the same direction at set intervals. Each shift in location of the transfer points delivers or removes liquid to or from a different bed within the chamber. In general, to simulate countercurrent movement of the adsorbent relative to the fluid stream within the chamber, the streams are shifted in the general direction of fluid flow, i.e. the downstream direction, within the chamber to simulate the solid adsorbent moving in the opposite, i.e. upstream, direction. The lines at these transfer points are reused as each stream enters or leaves the associated bed, and each line therefore carries one of the four process streams during some point of the cycle.

The art recognizes that the presence of residual compounds in the transfer lines can have detrimental effects on a simulated-moving-bed process. U.S. Pat. Nos. 3,201,491; 5,750,820; 5,884,777; 6,004,518; and 6,149,874 teach the flushing of the line used to deliver the feed stream to the adsorbent chamber as a means to increase the purity of the recovered extract or sorbate component. Such flushing avoids contamination of the extract stream with raffinate components of the feed remaining in this line when it is subsequently used to withdraw the extract stream from the chamber. U.S. Pat. No. 5,912,395 teaches flushing of the line just used to remove the raffinate stream in order to avoid contaminating feed with raffinate when this line is used to deliver the feed stream to the adsorbent chamber. All of these references teach flushing such lines back into the adsorbent chamber, thus increasing the separation load within the chamber. U.S. Pat. No. 7,208,651 discloses flushing away from the adsorbent chamber the contents of a transfer line which previously has been used to remove the raffinate stream with one or both of a feed mixture and a material withdrawn from the adsorption zone. The residual raffinate within the transfer line is flushed to join the raffinate stream as feed to a raffinate column. U.S. Pat. No. 6,149,874 discloses flushing residual feed from a common section of fluid distribution piping to a booster circuit.

One previous exemplary system utilized up to three flushes to handle residual fluid remaining in the transfer lines. A primary flush displaced residual extract from the transfer line just used to remove the extract stream with fluid from the desorption zone of the chamber just below the desorbent stream and directed it through a rotary valve to a transfer line just used to inject the feed stream. Because the volumes in the transfer lines were about equal, the extract-plus-desorbent fluid displaced the residual feed that had previously been in the transfer line into the adsorbent chamber just above the current feed stream position so that the residual feed could be separated with the feed stream within the adsorptive separation chamber and to avoid contamination of the extract stream with the residual feed remaining in the transfer line when the extract stream subsequently shifted to the transfer line previously occupied by the feed stream. Further, the residual extract from the primary flush used to displace the feed remained in the transfer line to be subsequently withdrawn by the extract stream to increase yield of the extract product.

The exemplary system sometimes included a secondary flush. The secondary flush utilized a flush of fluid, typically desorbent, through the transfer line and into the chamber immediately below the extract line. The secondary flush provided a "wash" of this transfer line with the desorbent to minimize the amount of contaminates, including raffinate, feed, and other components that may remain in the transfer line after the primary flush so that these materials were not withdrawn from the transfer line with the extract. Because this transfer line was previously flushed with desorbent and extract via the primary flush, the secondary flush was typically used in applications requiring high purity extract. The secondary flush would push the extract and desorbent material previously in the transfer line back into the adsorptive separation chamber. The secondary flush is an optional flush utilized to meet high purity demands of the extract product.

In some systems, a tertiary flush was also utilized. The tertiary flush included a flush of the transfer line previously occupied by the raffinate withdrawal stream. The tertiary flush was utilized to remove the residual raffinate from this transfer line to restrict this raffinate from being injected back into the adsorbent chamber with the feed upon subsequent arrival of the feed stream to the transfer line. Because the raffinate stream is depleted of the desired extract component, the tertiary flush was carried out so that the residual raffinate was not injected back into the adsorptive separation chamber, which would otherwise increase the separation demands in order to remove this additional raffinate material. The tertiary flush was accomplished by flushing the transfer line away from the adsorptive separation chamber with fluid from a port of the chamber adjacent to the transfer line.

SUMMARY OF THE INVENTION

According to various approaches, a process is provided for separating components in a feed stream by simulated countercurrent adsorptive separation. The process includes introducing a feed stream and a desorbent stream into two different ports via two different corresponding transfer lines along a multi-bed adsorptive separation chamber. The feed stream has at least one preferentially adsorbed component and at least one non-preferentially adsorbed component. The multi-bed adsorptive separation chamber has plurality of beds that are serially connected in fluid communication and comprising a predetermined number of spaced ports with corresponding transfer lines in fluid communication therewith for introducing and removing fluid into and from the adsorptive separation chamber. The process also includes withdrawing an extract stream and raffinate stream through two different ports of the multi-bed adsorptive separation chamber via two different corresponding transfer lines. The process according to this approach includes flushing an intermediate transfer line between the first intermediate transfer line and the extract stream transfer line away from the adsorptive separation chamber to remove residual fluid from intermediate transfer line. The process also includes directing the residual fluid flushed from the intermediate transfer line to a recycle stream to introduce the residual fluid into the adsorptive separation chamber. In this manner an amount of fluid required by the process may be reduced.

According to one approach, the process includes transferring residual fluid flushed from the intermediate transfer line to a bottoms portion of a raffinate fractionation column to be sent to the recycle stream. According to another approach, the process includes transferring the residual fluid flushed from the intermediate transfer line to a bottoms portion of an extract fractionation column to be sent to the recycle stream. According to these approaches, the residual fluid is not heated to an extract column bottoms outlet temperature thereby reducing energy consumption.

According to another approach, a process is provided for the separation of components in a feed stream comprising at least one preferentially adsorbed component and at least one non-preferentially adsorbed component by simulated countercurrent adsorptive separation that includes introducing a feed stream into a port of a multi-bed adsorbent chamber comprising a plurality of ports with corresponding transfer lines via a transfer line in fluid communication with the port. The process also includes flushing residual feed from the transfer line into the adsorptive separation chamber with a flushing fluid to fill the transfer line with the flushing fluid. The process according to this approach further includes flushing residual flushing fluid in the transfer line away from the adsorptive separation chamber with fluid from a purification zone of the adsorptive separation chamber adjacent to the port to fill the transfer line with the purification zone fluid. The process also includes withdrawing an extract stream from the adsorptive separation chamber through the transfer line that has a higher concentration of the preferentially adsorbed component than the feed stream and a lower concentration of the non-preferentially adsorbed component than the feed stream. In this manner, the transfer line is filled with purification zone fluid having a similar composition to the extract stream prior to withdrawal of the extract stream therethrough to restrict contamination of the extract stream with the non-preferentially adsorbed component.

Figure 1:
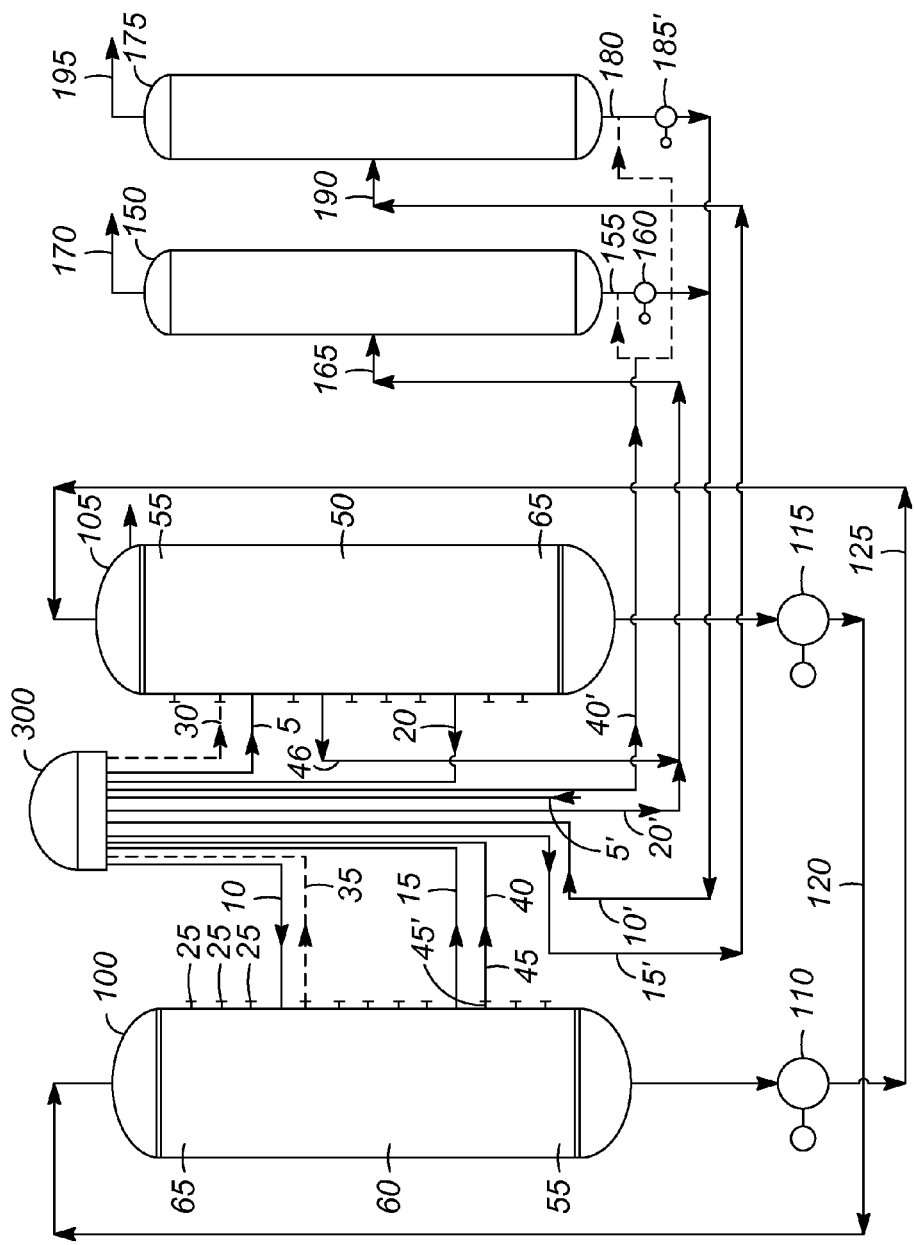
FIG. 1 is a simplified diagram of a simulated-moving-bed adsorption process in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION AND PREFERRED EMBODIMENTS

Adsorptive separation is applied to the recovery of a variety of hydrocarbon and other chemical products. Chemical separations using this approach which have been disclosed include the separation of mixtures of aromatics into specific aromatic isomers, of linear from nonlinear aliphatic and olefinic hydrocarbons, of either paraffins or aromatics from a feed mixture comprising both aromatics and paraffins, of chiral compounds for use in pharmaceuticals and fine chemicals, of oxygenates such as alcohols and ethers, and of carbohydrates such as sugars. Aromatics separations include mixtures of dialkyl-substituted monocyclic aromatics and of dimethyl naphthalenes. A major commercial application, which forms the focus of the prior references and of the following description of the present invention without so limiting it, is the recovery of para-xylene and/or meta-xylene from mixtures of $C_8$ aromatics, due to typically high purity requirements for these products. Such $C_8$ aromatics usually are derived within an aromatics complex by the catalytic reforming of naphtha followed by extraction and fractionation, or by transalkylation or isomerization of aromatics-rich streams in such complexes; the $C_8$ aromatics generally comprise a mixture of xylene isomers and ethylbenzene. Processing of $C_8$ aromatics using simulated-moving-bed adsorption generally is directed to the recovery of high-purity para-xylene or high-purity meta-xylene; high purity usually is defined as at least 99.5 wt.-% of the desired product, and preferably at least 99.7 wt.-%. It should be understood, that while the following detailed description focuses on the recovery of high-purity para-xylene from a mixed xylene and ethylbenzene stream, the invention is not so limited, and is also applicable for separating other components from a stream comprising two or more components. As used herein, the term preferentially adsorbed component refers to a component or components of a feed stream that are more preferentially adsorbed than one or more non-preferentially adsorbed components of the feed stream.

The invention normally is employed in an adsorptive separation process which simulates countercurrent movement of the adsorbent and surrounding liquid as described above, but it may also be practiced in a cocurrent continuous process, like that disclosed in U.S. Pat. Nos. 4,402,832 and 4,478,721. The functions and properties of adsorbents and desorbents in the chromatographic separation of liquid components are well-known, and reference may be made to U.S. Pat. No. 4,642,397, which is incorporated herein, for additional description of these adsorption fundamentals. Countercurrent moving-bed or simulated-moving-bed countercurrent flow systems have a much greater separation efficiency for such separations than fixed-bed systems, as adsorption and desorption operations are continuously taking place with a continuous feed stream and continuous production of extract and raffinate. A thorough explanation of simulated-moving-bed processes is given in the Adsorptive Separation section of the Kirk-Othmer ENCYCLOPEDIA OF CHEMICAL TECHNOLOGY at page 563.

Figure 13:
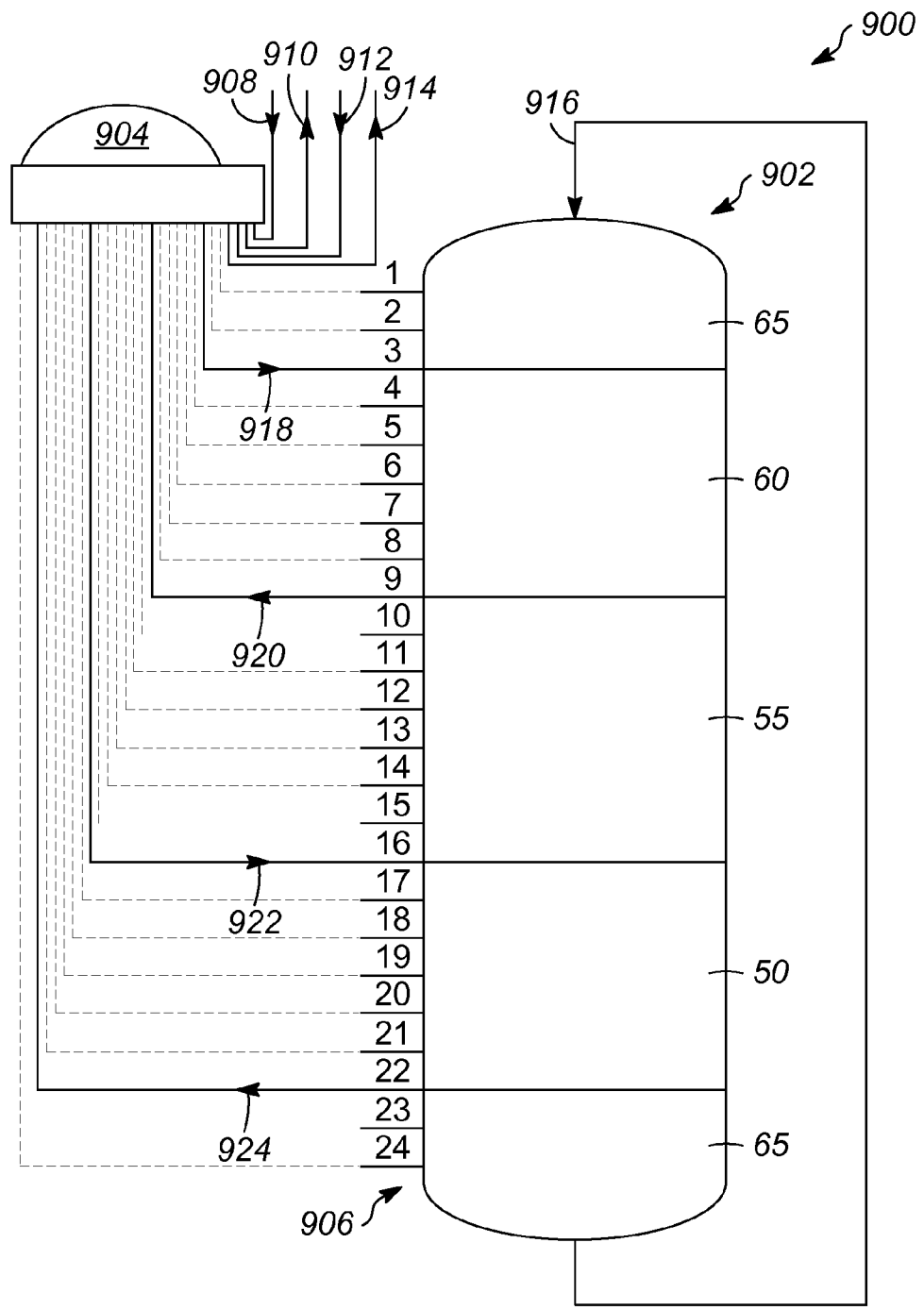
FIG. 13 is a simplified diagram of a Prior Art simulated-moving-bed adsorption process.

FIG. 1 is a schematic diagram of a simulated-moving-bed adsorption process in accordance with one aspect. The process sequentially contacts a feed stream 5 with adsorbent contained in the vessels and a desorbent stream 10 to separate an extract stream 15 and a raffinate stream 20. In the simulated-moving-bed countercurrent flow system, progressive shifting of multiple liquid feed and product access points or ports 25 down an adsorbent chamber 100 and 105 simulate the upward movement of adsorbent contained in the chamber. The adsorbent in a simulated-moving-bed adsorption process is contained in multiple beds in one or more vessels or chambers; two chambers 100 and 105 in series are shown in FIG. 1, although a single chamber 902 as illustrated in FIG. 13 or other numbers of chambers in series may be used. Each vessel 100 and 105 contains multiple beds of adsorbent in processing spaces. Each of the vessels has a number of ports 25 relating to the number of beds of adsorbent, and the position of the feed stream 5, desorbent stream 10, extract stream 15 and raffinate stream 20 are shifted along the ports 25 to simulate a moving adsorbent bed. Circulating liquid comprising desorbent, extract and raffinate circulates through the chambers through pumps 110 and 115, respectively. Systems to control the flow of circulating liquid are described in U.S. Pat. No. 5,595,665, but the particulars of such systems are not essential to the present invention. A rotary disc type valve 300, as characterized for example in U.S. Pat. Nos. 3,040,777 and 3,422,848, effects the shifting of the streams along the adsorbent chamber to simulate countercurrent flow. Although the rotary disc valve 300 is described herein, other systems and apparatus for shifting the streams along the adsorbent chamber are also contemplated herein, including systems utilizing multiple valves to control the flow of the streams to and from the adsorbent chamber 100 and/or 105 as for example, described in U.S. Pat. No. 6,149,874.

Figure 9:
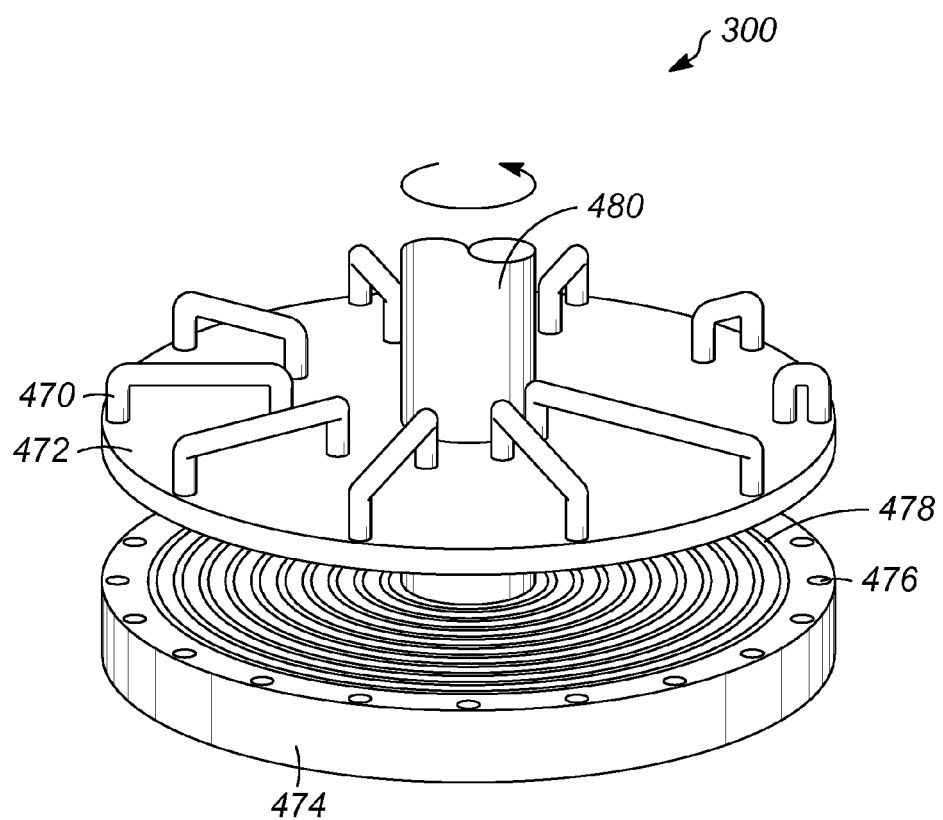
FIG. 9 is a perspective view of a rotary valve in accordance with various embodiments of the invention.

Referring to FIG. 9, a simplified exploded diagram of an exemplary rotary valve 300 for use in an adsorptive separation system and process is depicted. A base plate 474 includes a number of ports 476. The number of ports 476 equal the total number of transfer lines on the chamber(s). The base plate 474 also includes a number of tracks 478. The number of tracks 478 equal the number of net input, output, and flush lines for the adsorptive separation unit (not shown in FIG. 9). The net inputs, outputs, and flush lines are each in fluid communication with a dedicated track 478. Crossover lines 470 place a given track 478 in fluid communication with a given port 476. In one example, the net inputs include a feed input and a desorbent input, the net outputs include an extract output and a raffinate output, and the flush lines include between about one and about four flush lines. As the rotor 480 rotates as indicated each track 478 is placed in fluid communication with the next successive port 476 by crossover line 470. A seal sheet 472 is also provided.

The various streams involved in simulated-moving-bed adsorption as illustrated in the figures and discussed further below with regard to the various aspects of the invention described herein may be characterized as follows. A "feed stream" is a mixture containing one or more extract components or preferentially adsorbed components and one or more raffinate components or non-preferentially adsorbed components to be separated by the process. The "extract stream" comprises the extract component, usually the desired product, which is more selectively or preferentially adsorbed by the adsorbent. The "raffinate stream" comprises one or more raffinate components which are less selectively adsorbed or non-preferentially adsorbed. "Desorbent" refers to a material capable of desorbing an extract component, which generally is inert to the components of the feed stream and easily separable from both the extract and the raffinate, for example, via distillation.

The extract stream 15 and raffinate stream 20 from the illustrated schemes contain desorbent in concentrations relative to the respective product from the process of between 0% and 100%. The desorbent generally is separated from raffinate and extract components by conventional fractionation in, respectively, raffinate column 150 and extract column 175 as illustrated in FIG. 1 and recycled to a stream 10' by raffinate column bottoms pump 160 and extract column bottoms pump 185 to be returned to the process. FIG. 1 shows the desorbent as bottoms from the respective column, implying that the desorbent is heavier than the extract or raffinate; different commercial units for the separation of $C_8$ aromatics employ either light or heavy desorbents, and thus in some applications the desorbent may be separated at a different location along the fractionation columns 150 and 175. The raffinate product 170 and extract product 195 from the process are recovered from the raffinate stream and the extract stream in the respective columns 150 and 175; the extract product 195 from the separation of $C_8$ aromatics usually comprises principally one or both of para-xylene and meta-xylene, with the raffinate product 170 being principally non-adsorbed $C_8$ aromatics and ethylbenzene.

The liquid streams, e.g., the streams of feed 5, desorbent 10, raffinate 20, and extract 15 entering and leaving the adsorbent chambers 100 and 105 via the active liquid access points or ports 25 effectively divide the adsorbent chamber 100 and 105 into separate zones which move as the streams are shifted along the ports 25. It should be noted that while much of the discussion herein refers to FIG. 1 and the location of the streams in FIG. 1, FIG. 1 illustrates only a current location of the streams at a single step or a snapshot of the process as the streams typically shift downstream at different steps of a cycle. As the streams shift downstream, the fluid composition and the corresponding zones shift downstream therewith. In one approach, the position of the streams with regard to the access points or ports 25 of the adsorptive separation chambers 100 and 105 remain generally constant with regard to one another as they synchronously progress downstream along the ports 25. In one example, the streams each progress a single port 25 downstream for each step and each stream occupies each port 25 one time during an entire cycle. According to one example, the streams are stepped simultaneously to subsequent ports 25 by rotating a rotary valve 300, and are maintained at a particular port 25 or step for a predetermined step-time interval. In one approach, there are between about 4 and 100 ports 25, between about 12 and 48 ports in another approach, and between about 20 and 30 ports in yet another approach, and an equal number of corresponding transfer lines. In one example, the adsorptive separation chamber or chambers 100 and 105 include about 24 ports and each stream is shifted to each of the 24 ports 25 during a complete cycle so that each stream occupies each port 25 and corresponding transfer line during the cycle. In this example, a cycle may be between about 20 and about 40 minutes in one approach and between about 22 and 35 minutes in another approach. In one approach, a step-time interval is between about 30 seconds and about two minutes. In another approach, the step-time interval is between about 45 seconds and about one minute thirty seconds. In yet another approach, the step-time interval is between about 50 seconds and about one minute and 15 seconds. An example of a typical step-time interval may be about 1 minute.

Figure 8:
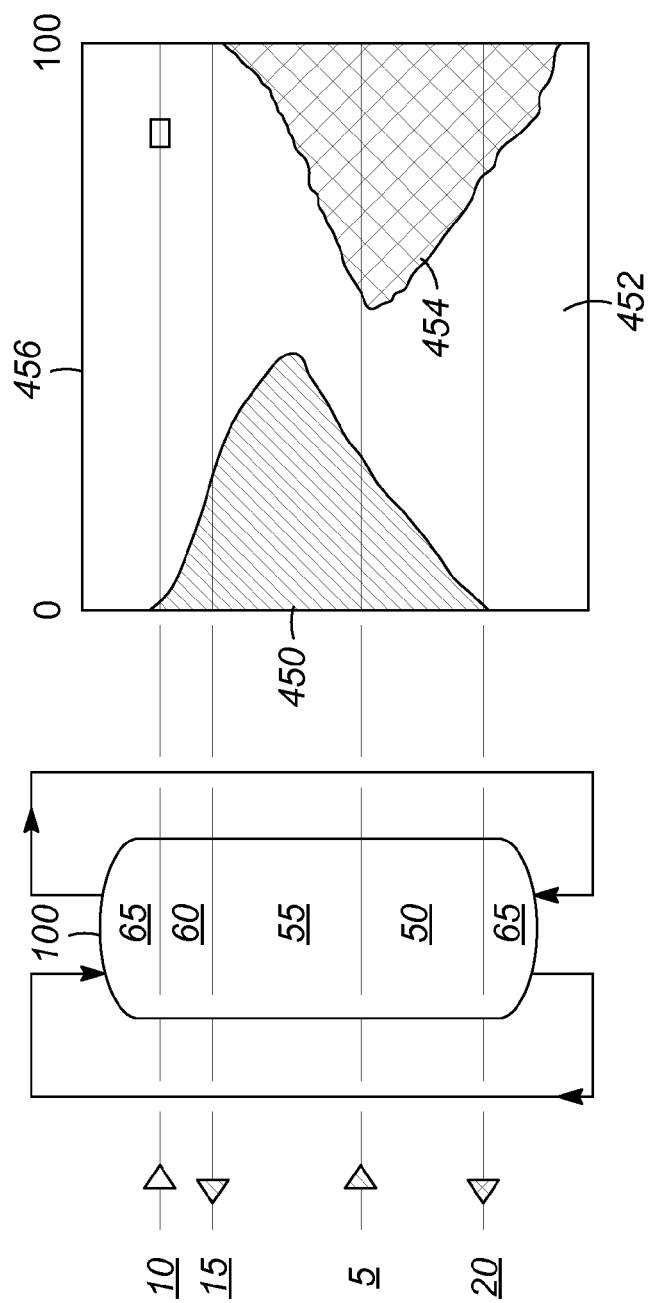
FIG. 8 is a compositional diagram of fluid within a simulated-moving-bed adsorptive separation chamber in accordance with various embodiments of the invention.

With this in mind, FIG. 8 illustrates a snapshot of the compositional profile of the fluid within an adsorptive separation chamber (a single adsorptive separation chamber 100 is illustrated in FIG. 8 for simplicity) and the corresponding zones into which the adsorptive separation chamber 100 is divided. The adsorption zone 50 is located between the feed inlet stream 5 and the raffinate outlet stream 20. In this zone, the feed stream 5 contacts the adsorbent, an extract component is adsorbed, and a raffinate stream 20 is withdrawn. As illustrated in the figure, the raffinate stream 20 may be withdrawn at a location where the composition includes raffinate fluid 454 and little if any extract fluid 450. Immediately upstream with respect to fluid flow is the purification zone 55, defined as the adsorbent between the extract outlet stream 15 and the feed inlet stream 5. In the purification zone 55, the raffinate component is displaced from the nonselective void volume of the adsorbent and desorbed from the pore volume or surface of adsorbent shifting into this zone by passing a portion of extract stream material leaving the desorption zone 60. The desorption zone 60, upstream of the purification zone 55, is defined as the adsorbent between the desorbent stream 10 and the extract stream 15. The desorbent passing into this zone displaces the extract component which was adsorbed by previous contact with feed in the adsorption zone 50. The extract stream 15 may be withdrawn at a location of the chamber 100 that includes extract fluid 450 and little if any raffinate fluid 454. A buffer zone 65 between the raffinate outlet stream 20 and the desorbent inlet stream 10 prevents contamination of the extract, in that a portion of the desorbent stream enters the buffer zone to displace raffinate material present in that zone back into the adsorption zone 50. The buffer zone 65 contains enough adsorbent to prevent raffinate components from passing into the desorption zone 60 and contaminating the extract stream 15.

Each of the zones described above generally are effected through multiple compartments or "beds" as described in U.S. Pat. No. 2,985,589. The positions of the various streams described are structurally separated from one another by a horizontal liquid collection/distribution grid. Each grid is connected to a transfer line defining a transfer point at which process streams enter and leave the adsorbent chamber. This arrangement facilitates the distribution of fluids within the chamber through eliminating channeling and other inefficiencies, prevents convective back-mixing of fluid in a direction opposite to that of primary fluid flow, and prevents migration of adsorbent through the chamber. Each of the zones described above usually comprises a plurality of 2 to 10, and more usually 3 to 8, beds. A typical simulated-moving-bed adsorption unit comprises 24 beds of adsorbent.

It is readily apparent in FIG. 1 that when a transfer line at an access point 25 which is being used to transport a particular stream into or out of the adsorbent chamber is left idle at the end of a step it will remain full of the compounds forming that stream until these compounds are removed from the line by a second flowing stream. In this regard, it should be noted that only active transfer lines, i.e. those lines presently facilitating flow of fluid therethrough, are illustrated in FIG. 1, although intermediate transfer lines are present at each of the ports 25 along the chambers 100 and 105 to facilitate fluid flow upon shifting of the fluid streams to subsequent ports 25. The residual fluid or compounds left in the now unused transfer line after a stream shifts to a subsequent transfer line, will therefore be either withdrawn from the process as the initial part of a process stream removed from the process or forced into the adsorbent chamber when the transfer line carries a stream into the adsorbent chamber. FIG. 13 illustrates a previous system showing unused transfer lines as dashed lines and transfer lines currently occupied by a stream, e.g. stream 920 as solid lines extending from ports of the adsorptive separation chamber 902.

Returning to FIG. 1, as described above, the presence of residual fluid in the transfer lines can have deleterious effects on the performance of a simulated-moving-bed adsorptive separation process. For example, residual raffinate in a transfer line which previously had been used to remove the raffinate stream 20 from the adsorbent chamber may be flushed into the adsorbent chamber 105 with the feed stream 5 when it shifts to that transfer line in a subsequent step. Similarly, residual feed in a transfer line which previously had been used to introduce the feed stream 5 to the adsorbent chamber may be removed from the transfer line with the extract stream 15 when it shifts to that transfer line in a subsequent step. Likewise, residual extract in a transfer line which previously had been used to remove the extract stream from the adsorbent chamber may be flushed back into the adsorbent chamber 100 with the desorbent stream 10 when it subsequently arrives at that transfer line.

In accordance with one aspect, a primary flush of the process and system includes a primary flush in 30, which flushes residual feed within the transfer line previously occupied by the feed stream 5 into the adsorptive separation chamber 105, and more particularly into the purification zone 55. The primary flush in 30 may advantageously be directed to the transfer line of the purification zone 55 near the transfer line currently occupied by the feed stream 5 to introduce the residual feed into the adsorptive separation chamber 105 near the feed stream 5 so that the residual feed can be separated therein. In one example, the primary flush in 30 may be directed to a transfer line of the purification zone 55 within two transfer lines of the feed stream 5, and more preferably to a transfer line adjacent to the feed stream 5, as illustrated in FIG. 1. In one approach, the primary flush in 30 utilizes flush fluid including primarily the preferentially adsorbed component, desorbent, and/or inert components. In other words, the flush fluid preferably includes little if any of the non-preferentially adsorbed component of the feed, to restrict contamination of the extract stream 15 when the extract stream arrives at the transfer line during a subsequent step.

The primary flush of the process and system may include a primary flush out 35 to flush the residual extract fluid from the transfer line previously occupied by the extract stream away from the adsorbent chamber. The extract fluid along with the primary flush flushing fluid is then transferred to the primary flush in 30 transfer line as the flush fluid and is utilized to flush the residual feed from the transfer line previously occupied by the feed stream into the purification zone of the adsorptive separation chamber 105 as described previously. In one approach, the primary flush out 35 utilizes fluid from the desorption zone 60 of the chamber 100 to flush the transfer line that includes primarily desorbent. In this manner, after the primary flush out 35 flushes the residual extract fluid within the transfer line previously occupied by the extract stream 15, very little extract fluid remains in the transfer line. Advantageously, by coupling the primary flush out 35 with the primary flush in 30, residual fluid in the transfer lines can be used for flushing other transfer lines, reducing the overall amount of fluid required by the process and increasing the yield of the process by capturing these fluids, while achieving the transfer line flushing purposes discussed previously. In addition, the pairing of the primary flushes provides the flush fluid for the primary flush in 30, which includes primarily desorbent and the preferentially adsorbed component from the residual extract fluid. Likewise, this provides a flush fluid for the primary flush in 30 that includes very little of the non-preferentially adsorbed component. In one example, the flush fluid for the primary flush in 30 includes more than about 99 wt. % desorbent and the preferentially adsorbed component. In another example, the flush fluid includes less than about 0.005 wt. % of the non-preferentially adsorbed component(s).

According to one approach, a secondary flush 40 is used to flush residual fluid from a transfer line that will subsequently be occupied by the extract stream 15 to remove contaminants from the transfer line. The secondary flush 40 advantageously provides increased purity of the extract stream by removing contaminants from the transfer line before the transfer line is used to withdraw the extract stream 15 therethrough. Previous systems utilized a flush of desorbent into the transfer line and toward the adsorptive separation chamber to flush the contents of the transfer line that will subsequently be used for withdrawal of the extract stream. This flush is sent through the transfer line toward the adsorptive separation chamber and into the purification zone of the adsorptive separation chamber to provide purification thereof.

It has been identified that the secondary flush of previously systems discussed previously created a utilities or energy penalty. Specifically, because the secondary flush 40 uses desorbent to flush the residual preferentially adsorbed component/desorbent fluid in the transfer line into the adsorptive separation chamber, this transfer line includes almost exclusively desorbent after the secondary flush. The residual desorbent within this transfer line is subsequently withdrawn as an initial surge of fluid by the extract stream prior to the removal of extract. The extract stream, including this surge of residual desorbent, is directed to the extract fractionation column 175, where it is fractionated out as a bottoms product and recycled with desorbent recycle stream to the first chamber 100. However, in order to enter the column 175, the surge of residual desorbent within the transfer line at the beginning of the removal of the extract must also be heated prior to entering the extract column 175 for fractionation. For example, when para-xylene is being separated from a feed stream of mixed xylenes, the desorbent withdrawn with the extract stream is heated from about 150° C. to about 300° C., resulting in an energy or utilities penalty. In other words, because this initial slug of desorbent contains very little if any of the desired extract product, it requires a substantial energy input to increase the temperature to the extract fractionation column bottoms outlet temperature while not providing a benefit in terms of increased extract product yield.

In order to avoid this utilities and energy penalty, according to one aspect a secondary flush 40 flushes residual fluid from the transfer line 45 away from the adsorptive separation chamber 100, the opposite of previous systems, so that residual desorbent does not build up within the transfer line 45. It should be noted that the transfer line 45 is used for the secondary flush 40 in the step illustrated in FIG. 1, however, during previous or subsequent steps the secondary flush 40 may shift along with the streams and be used to remove residual fluid from other transfer lines. More specifically, rather than using a desorbent stream to flush the residual fluid from the transfer line 45, which may include primarily the preferentially adsorbed component and desorbent remaining in the transfer line after the primary flush in 30, fluid from the purification zone, adjacent to the transfer line port 45' corresponding to the transfer line is used to flush the residual fluid away from the adsorbent chamber 100. The secondary flush stream may then be transferred for further processing. In one approach, the secondary flush is sent by a line 40' to a fluid recycle line 10'. The fluid recycle line 10' may include primarily desorbent that is separated via the fractionation columns 150 and 175 and recycled back to the adsorptive separation chamber 100 where it is reused in the process. In one approach, the secondary flush stream is sent via line 40' to a bottoms portion 155 of the raffinate fractionation column 150 where it is combined with the desorbent separated by the raffinate fractionation column 150 and sent to the fluid recycle line 10' via a raffinate bottoms pump 160. In another approach the secondary flush stream is sent via line 40' to a bottoms portion 180 of the extract fractionation column 175 where it is combined with the desorbent separated by the extract fractionation column 175 and sent to the fluid recycle line 10' via a extract bottoms pump 185.

Because this fluid from the purification zone 55 is similar in composition to the extract stream 15 that will be subsequently withdrawn from the transfer line 45, the residual fluid remaining in the bed line after the modified secondary flush 40 will advantageously be similar in composition to the desired extract composition. To this end, in one example the transfer line 45 is flushed by the secondary flush 40 within two transfer lines or ports from the transfer line currently occupied by the extract line 15, and more preferably within one transfer line or port from the transfer line currently occupied by the extract line 15, since purification zone fluid adjacent to ports near the extract transfer line will have compositions most similar to the extract stream 15. In one example, the purification zone fluid has more than about 99% desorbent and preferentially adsorbed component. In another example, the purification zone fluid has less than about 0.005% of the non-preferentially adsorbed component(s). Further, when a primary flush in 30 is used to flush residual feed as described previously, the secondary flush 40 according to one approach is positioned between the transfer line currently occupied by the extract stream 15 and the transfer line currently occupied by the primary flush in 30 so that the transfer line 45 is primarily filled with residual fluid from the primary flush in 30 rather than the feed stream 5. This approach advantageously reduces the extent of contamination of the extract stream 15 with residual feed.

Further, in one approach, fluid within the transfer line 45 that will subsequently be withdrawn with the extract stream 15 will be sent to the extract fractionation column 175 to be separated via a distillation. The residual fluid within the transfer line 45 that is sent with the extract stream to the extract fractionation column 175 is heated within extract fractionation column 175. Because this residual fluid is similar in composition to the extract stream 15 fractionation of this fluid will result in increased recovery of the desired extract product 195. Thus, unlike prior systems, fluid remaining in the transfer line 45 from the secondary flush 40 that is subsequently taken up with the extract stream 15 and sent to the extract fractionation column 175 will not result in an unnecessary utilities penalty, because distillation of this fluid will result in additional yield of the desired extract product 195 rather than primarily desorbent.

Figure 2:
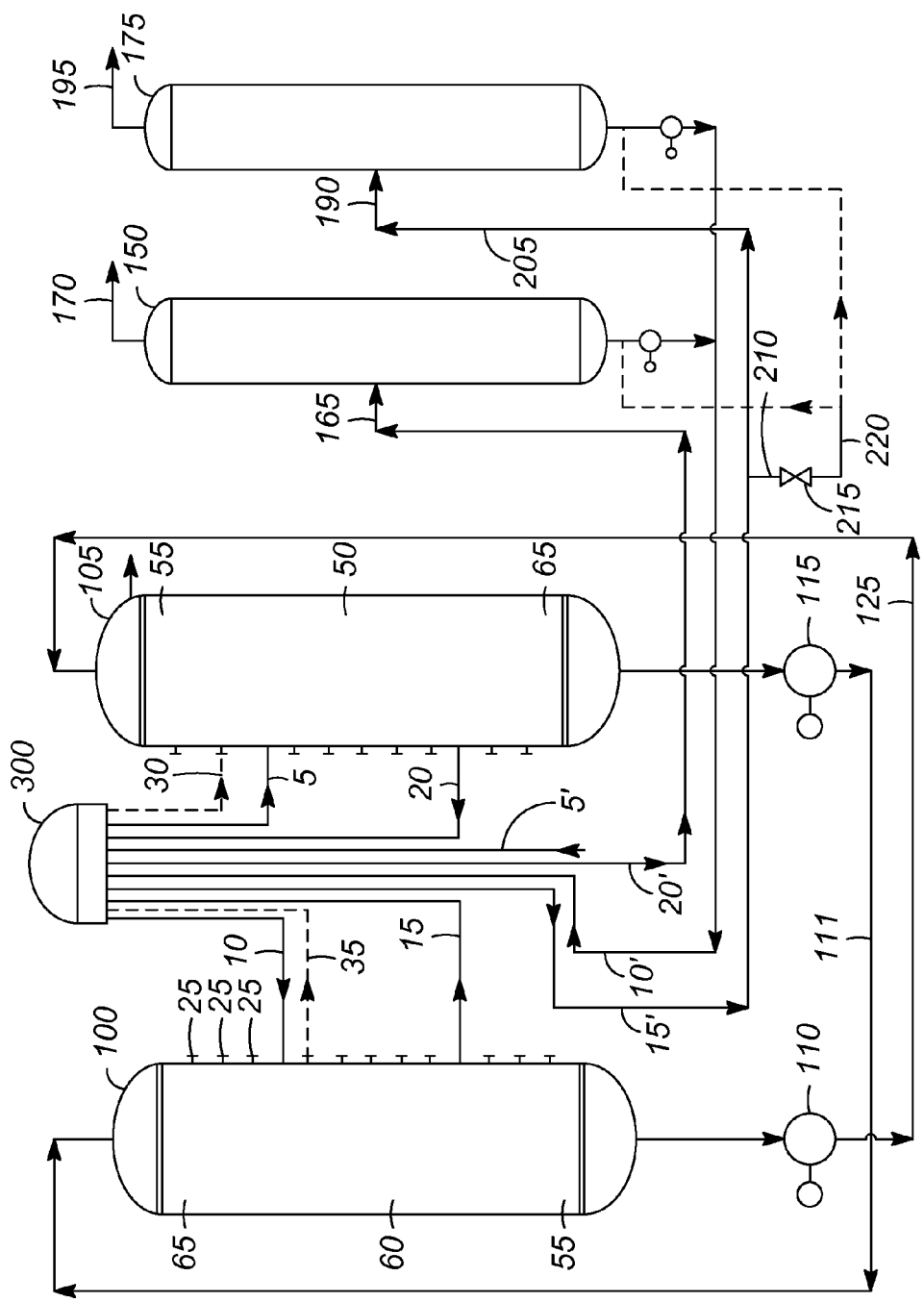
FIG. 2 is a simplified diagram of a simulated-moving-bed adsorption process in accordance with various embodiments of the invention.

In accordance with another aspect illustrated in FIG. 2, the extract stream 15 may be withdrawn through a transfer line during a step as previously described. In this approach, the extract stream 15 is withdrawn along with residual fluid remaining in the transfer line so that the extract stream flushes the residual fluid away from the transfer line. An initial slug of the extract stream, including at least a portion of the residual fluid, is directed through the transfer line to a first destination. A subsequent portion of the extract stream is then directed through the transfer line to a second destination. At least a portion of the residual fluid within the transfer line is directed to the first destination. In one example at least about 90% of the residual fluid is directed to the first destination. In another example, at least about 95% of the residual fluid is directed to the first destination. In one approach, the second destination is an inlet 190 of the extract fractionation column 175. The first destination may be a recycle line 10' for recycling the extract stream and the portion of the residual fluid to the adsorptive separation chamber 100.

As illustrated in FIG. 2, a primary flush in 30 may be utilized to flush residual feed fluid remaining in the transfer line previously occupied by the feed stream 5 into the adsorptive separation chamber 105 as described previously to restrict the residual feed fluid from being withdrawn with the extract stream as the residual fluid in the transfer line when the extract stream 15 arrives at the transfer line in a subsequent step. The flushing fluid preferably includes primarily desorbent and/or the preferentially adsorbed component and includes very little of the non-preferentially adsorbed component so that the residual fluid remaining in the transfer line after the primary flush in 30 includes very little of the non-preferentially adsorbed component. In one approach, the flushing fluid includes less than about 1% of the non-preferentially adsorbed component and in another example includes less than about 0.005% of the non-preferentially adsorbed component. As described previously, residual extract remaining in a transfer line previously occupied by the extract stream 15 may be flushed from the transfer line via a primary flush out 35, and the residual extract fluid may be transferred to the primary flush in 30 transfer line to be used as the flushing fluid for the primary flush in 30. The residual extract fluid may be flushed via the primary flush out 35 by withdrawing fluid from the desorption zone 60 adjacent to the port 25 in communication with the primary flush out 35 transfer line. In this regard, the residual fluid within the transfer line when the extract stream 15 is shifted thereto, may include primarily residual extract and flushing fluid withdrawn from the desorption zone 60 via the primary flush out 35, e.g. residual extract and desorbent.

Turning to more of the particulars in FIG. 2, according to this approach, the extract stream 15 is withdrawn through the transfer line including the residual fluid so that an initial slug of the extract stream will include the residual fluid that remained in the transfer line prior to the arrival of the extract stream 15. As mentioned previously, this initial slug of the extract stream may be sent to a recycle line 10' to be recycled back to the adsorptive separation chamber 100. To this end, the initial slug of the extract stream may be sent to a raffinate fractionation column bottoms portion 155. At the raffinate column bottoms portion 155 the slug of fluid is combined with fluid exiting the bottom of the raffinate fractionation column 150, which in one example includes primarily desorbent that has been separated in the raffinate fractionation column 150. A raffinate column bottoms pump 160 may be used to direct this slug of fluid and the desorbent back to the adsorptive separation chamber 100 through the recycle line 10'. Alternatively, the initial slug of the extract stream may be sent to an extract fractionation column bottoms portion 180. At the extract column bottoms portion 180 the slug of fluid is combined with fluid exiting the bottom of the extract fractionation column 175, which in one example includes primarily desorbent that has been separated in the extract fractionation column 175. An extract column bottoms pump 185 may be used to direct this slug of fluid and the desorbent back to the adsorptive separation chamber 100 through the recycle line 10'.

In this manner, at least a portion of the residual fluid withdrawn with the extract stream 15 is not directed to the extract fractionation column inlet 190. Because the residual fluid in the transfer line from the primary flush 30 will contain a greater percentage of desorbent than the extract stream 15, this excess desorbent is advantageously not separated in the extract fractionation column 175. Because fluid entering the extract fractionation column inlet 190 is heated, if the excess desorbent in the residual fluid was introduced into the extract fractionation column 175 it would be heated to the bottoms outlet temperature without providing additional yield of the extract product, and thus incurring an energy penalty. Thus, by diverting the initial slug of fluid so that excess desorbent is not introduced into the extract fractionation column 175, the amount of energy required by the system is reduced.

According to one aspect, the extract stream 15 is withdrawn from the adsorptive separation chamber 100 and sent along a transfer line 15'. In one approach a rotary valve 300 is provided so that the extract stream 15 is withdrawn through the transfer line and directed to the rotary valve where it is combined with a single extract transfer line 15' as illustrated in FIG. 2, although other configurations are contemplated herein, including providing a dedicated extract transfer line 15' for each transfer line of the adsorptive separation chambers 100 and 105. The transfer line 15' may have one extract inlet line 205 in fluid communication with the extract fractionation column inlet 190. The transfer line 15' may have another bottoms portion line 210 in communication with one or both of the extract column bottoms portion 180 and the raffinate column bottoms portion 155. A valve 215 may be provided for diverting the flow of the extract stream 15 between the extract column inlet line 205 and the extract column bottoms portion line 210. In this manner, the process includes moving the valve 215 to a first position to direct the initial portion extract stream 15 including at least a portion of the residual fluid through the extract column bottoms portion line 210 to one of the extract column bottoms portion 180 and the raffinate column bottoms portion 155. In this example, the process includes diverting the valve 215 to a second position to direct the extract stream 15 through the extract column inlet line 205 and toward the extract fractionation column inlet 190 for separation of the extract stream 15 therein.

In accordance with one aspect, the extract stream, including at least a portion of the residual fluid flushed from the transfer line by the extract stream, is directed to the first destination, e.g. one or both of the extract column and the raffinate column bottoms portions 180 and 155 for a first predetermined time or predetermined portion of a step-time interval (when the extract stream occupies a current transfer line). The extract stream is then directed to the second destination, e.g. the inlet of the extract fractionation column 175 for a second predetermined time or predetermined portion of the step-time interval. The first predetermined time may be selected based on a flow rate of the extract stream to flush a predetermined amount of the residual fluid in the transfer line to the second destination or a predetermined amount of fluid to the second destination. In one example, the first predetermined time may be sufficient to direct a volume of fluid of about 50% to about 250% of a volume of the transfer line and associated valving, and in another example from about 80% to about 150% of the volume of the transfer line and associated valving, to the first destination. In one approach, the second predetermined time may be the remainder of the step-time interval so that the extract stream 15 is directed to the extract column inlet 190 for the remainder of the step-time interval for separation of the extract stream 15 in the extract fractionation column 175. The predetermined times may also be selected to direct all or at least a portion of the residual fluid in the transfer line to the first destination so that the residual fluid is not introduced into the extract fractionation column to provide energy savings. Similarly, a first predetermined volume of the extract stream may be directed to the first destination and a second predetermined volume of the extract stream may be direct to the second destination. The first predetermined volume may be the same as described above for the first predetermined time. The second predetermined volume may be the remaining volume of the extract stream withdrawn through the transfer line during the step-time interval. In one example, the first predetermined time is between about 10% and about 90% of the step-time interval. The second predetermined time in this example is between about 10% and about 90% of the step time interval. In another example, the first predetermined time is between about 20% and about 40% of the step-time interval. The second predetermined time in this other example is between about 60% and about 80% of the step time interval.

In another approach, the process includes monitoring the composition of the extract stream, including any residual fluid therein to determine a quantity or percentage of a component within the composition. For example, the component may be one of the preferentially adsorbed component, a desorbent component, or the non-preferentially adsorbed component. The process according to this approach includes directing the extract stream 15 and any residual fluid to the first destination when the composition includes the component at a first predetermined level and directing the extract stream 15 to the second destination when the composition includes the component at a second predetermined level. For example, the process may include monitoring the composition of the extract stream 15 to determine the amount of the desorbent present in the stream. According to this example, the process may include directing the extract stream to the first destination when the amount of desorbent is above a threshold level and directing the extract stream to the second destination when the amount of desorbent is below the threshold level. In this manner, the amount of desorbent sent to the extract fractionation column inlet 190 may be reduced.

Advantageously, according to this approach, the secondary flush 40 of previous systems may be omitted. In this manner, the process may be used with one less active transfer line. For example, the process may use only six or seven transfer lines rather than seven or eight transfer lines, as was required in previous systems. In one approach, the process may use a rotary valve 300 with only six or seven tracks, including tracks for the extract, raffinate, feed, and desorbent streams, and also the primary flush out 35, the primary flush in 30, and optionally a tertiary flush 46. This approach advantageously allows existing adsorptive separation systems with six and seven track rotary valves to be retrofitted to utilize the invention according to this approach.

Figure 3:
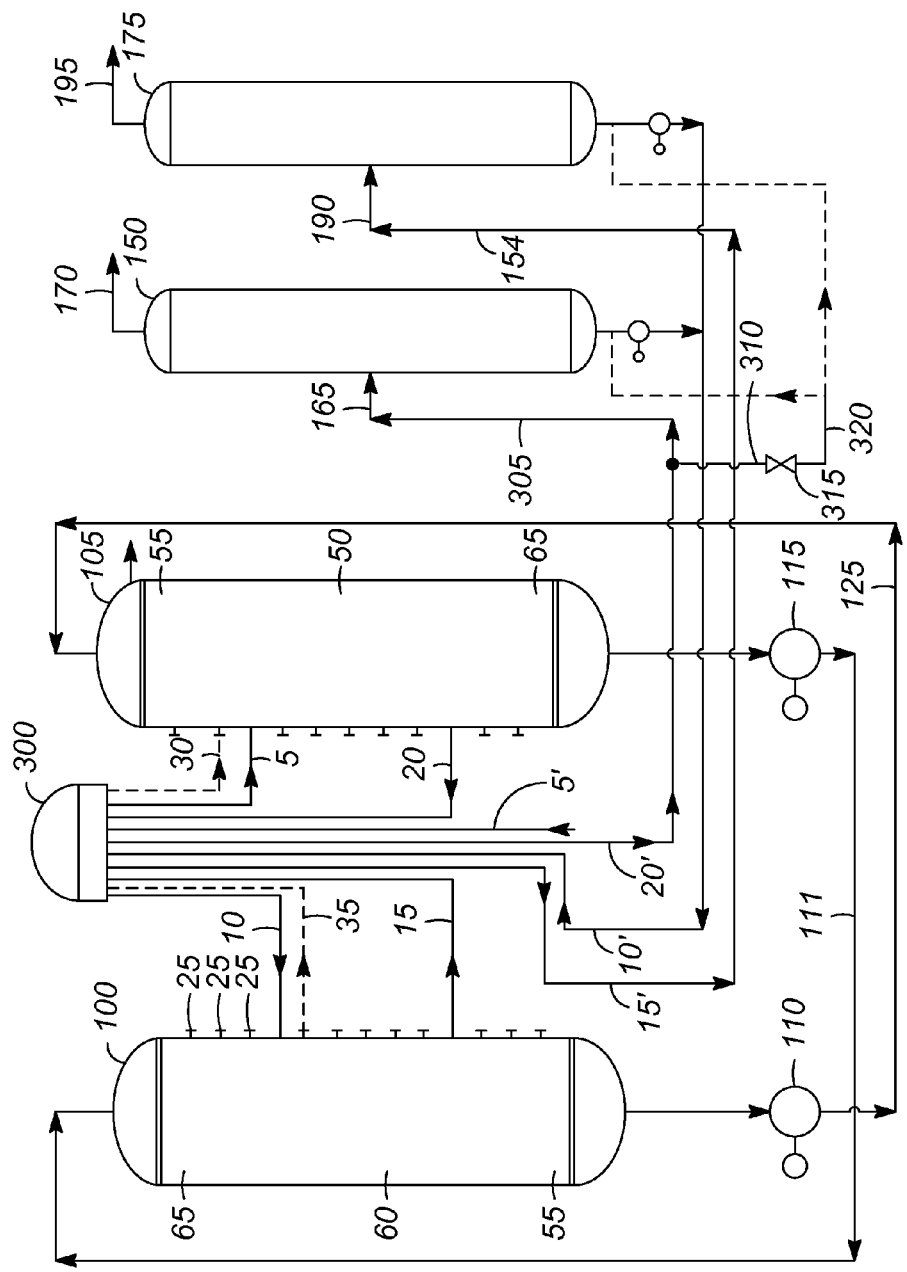
FIG. 3 is a simplified diagram of a simulated-moving-bed adsorption process in accordance with various embodiments of the invention.

Turning now to FIG. 3, an adsorptive separation system and process in accordance with another aspect is illustrated. According to this aspect, the raffinate stream 20 may be withdrawn through a transfer line during a step as previously described. In this approach, the raffinate stream 20 is withdrawn along with residual fluid remaining in the raffinate stream transfer line so that the raffinate stream 20 flushes the residual fluid away from the transfer line. This aspect is similar to that described above and illustrated in FIG. 2 in that an initial slug of the raffinate stream is directed to a first destination. A subsequent portion of the raffinate stream is then directed to a second destination. At least a portion of the residual fluid within the transfer line is directed to the first destination. In one example at least about 90% of the residual fluid is directed to the first destination. In another example, at least about 95% of the residual fluid is directed to the first destination. In one aspect, the second destination is an inlet 165 of the raffinate fractionation column 150. The first destination may be a recycle line 10' for recycling the raffinate stream and the portion of the residual fluid to the adsorptive separation chamber 100. In this regard, by recycling a portion of the fluid back to the adsorptive separation chamber 100 the amount of fluid processed by the raffinate fractionation column 150.

As illustrated in FIG. 3, in one approach, the transfer line occupied by the raffinate stream 20 was previously occupied by the desorbent stream 10. In this regard, the transfer line may include primarily residual desorbent fluid when the raffinate stream arrives at the transfer line in a subsequent step.

Turning to more of the particulars in FIG. 3, according to this aspect, the raffinate stream 20 is withdrawn through the transfer line including the residual fluid so that an initial slug of the raffinate stream will include the residual fluid that remained in the transfer line prior to the arrival of the raffinate stream 20. As mentioned previously, this initial slug of the raffinate stream may be sent to a recycle line 10' to be recycled back to the adsorptive separation chamber 100. To this end, similar to the approach described previously with regard to FIG. 2, the initial slug of the raffinate stream 20 may be sent to a raffinate fractionation column bottoms portion 155. At the raffinate column bottoms portion 155 the slug of fluid is combined with fluid exiting the bottom of the raffinate fractionation column 150, which in one example includes primarily desorbent that has been separated in the raffinate fractionation column 150. A raffinate column bottoms pump 160 may be used to direct this slug of fluid and the desorbent back to the adsorptive separation chamber 100 through the recycle line 10'. Alternatively, the initial slug of the raffinate stream 20 may be sent to an extract fractionation column bottoms portion 180. At the extract column bottoms portion 180 the slug of fluid is combined with fluid exiting the bottom of the extract fractionation column 175, which in one example includes primarily desorbent that has been separated in the extract fractionation column 175. Similarly, an extract column bottoms pump 185 may be used to direct this slug of fluid and the desorbent back to the adsorptive separation chamber 100 through the recycle line 10'.

In this manner, at least a portion of the residual fluid withdrawn with the raffinate stream 20 is not directed to the raffinate fractionation column inlet 165. Because the residual fluid in the transfer line will contain a greater percentage of desorbent than the raffinate stream fluid, this excess desorbent is advantageously not sent to and separated in the raffinate fractionation column 150. Because fluid entering the raffinate fractionation column inlet 165 is heated in the column, if the excess desorbent in the residual fluid was introduced into the raffinate fractionation column 150 it would be heated without providing additional yield of the extract product, and thus incurring an energy penalty. Thus, by diverting the initial slug of fluid so that excess desorbent is not introduced into the raffinate fractionation column 150, the amount of energy required by the system is reduced.

In one approach, the raffinate stream 20 is withdrawn from the adsorptive separation chamber 100 and sent along a transfer line 20'. In one approach a rotary valve 300 is provided so that the raffinate stream 20 is withdrawn through the transfer line and directed to the rotary valve 300 where it is combined with a single raffinate transfer line 20' as illustrated in FIG. 3, although other configurations are contemplated herein, including providing a dedicated raffinate transfer line 20' for each transfer line of the adsorptive separation chambers 100 and 105. The transfer line 20' may have one raffinate inlet line 305 in fluid communication with the raffinate fractionation column inlet 165. The transfer line 20' may have another bottoms portion line 310 in fluid communication with one or both of the extract column bottoms portion 180 and the raffinate column bottoms portion 155. A valve 315 may be provided for diverting the flow of the raffinate stream 20 between the raffinate column inlet line 305 and the raffinate column bottoms portion line 310. In this manner, the process includes moving the valve 315 to a first position to direct the initial portion raffinate stream 20 including at least a portion of the residual fluid through the raffinate column bottoms portion line 310 to one of the extract column bottoms portion 180 and the raffinate column bottoms portion 155. In this example, the process includes moving the valve 315 to a second position to direct the raffinate stream 20 through the raffinate column inlet line 305 and toward the raffinate fractionation column inlet 165 for separation of the raffinate stream 20 therein.

In one aspect, the raffinate stream 20, including at least a portion of the residual fluid flushed from the transfer line by the raffinate stream, is directed to the first destination, e.g. one or both of the extract column and the raffinate column bottoms portions 180 and 155 for a first predetermined time or predetermined portion of a step-time interval (when the raffinate stream occupies a current transfer line). The raffinate stream is then directed to the second destination, e.g. the raffinate fractionation column inlet 165 for a second predetermined time or predetermined portion of the step-time interval. The first predetermined time may be selected based on a flow rate of the raffinate stream 20 to flush a predetermined amount of the residual fluid in the transfer line to the second destination or a predetermined amount of overall fluid to the second destination. In one example, the first predetermined time may be sufficient to direct a volume of fluid of about 50% to about 250% of a volume of the transfer line and associated valving, and in another example from 80% to about 150% of the volume of the transfer line and associated valving, to the first destination. In one approach, the second predetermined time may be the remainder of the step-time interval so that the raffinate stream 20 is directed to the raffinate column inlet 165 for the remainder of the step-time interval for separation of the raffinate stream 20 in the raffinate fractionation column 150. The predetermined times may also be selected as other values in order to direct all or at least a portion of the residual fluid in the transfer line to the first destination so that the residual fluid is not introduced into the raffinate fractionation column 150 to provide energy savings. In one example, the first predetermined time is between about 10% and about 90% of the step-time interval. The second predetermined time in this example is between about 10% and about 90% of the step time interval. In one example, the first predetermined time is between about 10% and about 30% of the step-time interval. The second predetermined time in this example is between about 70% and about 90% of the step time interval. Similarly, a first predetermined volume of the raffinate stream may be directed to the first destination and a second predetermined volume of the raffinate stream may be direct to the second destination. The first predetermined volume may be the same percentage of the volume of the transfer line and associated valving as described above for the first predetermined time. The second predetermined volume may be the remaining volume of the raffinate stream withdrawn through the transfer line during the step-time interval.

In another aspect, the process includes monitoring the composition of the raffinate stream 20, including any residual fluid therein to determine a quantity or percentage of a component within the composition. For example, the component may be one of the preferentially adsorbed component, a desorbent component, or the non-preferentially adsorbed component. The process according to this approach includes directing the raffinate stream 20 and any residual fluid to the first destination when the composition includes the component at a first predetermined level and directing the raffinate stream 20 to the second destination when the composition includes the component at a second predetermined level. For example, the process may include monitoring the composition of the raffinate stream to determine the amount of the desorbent present in the stream. According to this example, the process may include directing the raffinate stream to the first destination when the amount of desorbent is above a threshold level and directing the raffinate stream to the second destination when the amount of desorbent is below the threshold level. In this manner, the amount of desorbent sent to the raffinate fractionation column inlet 165 may be reduced.

Figure 4:
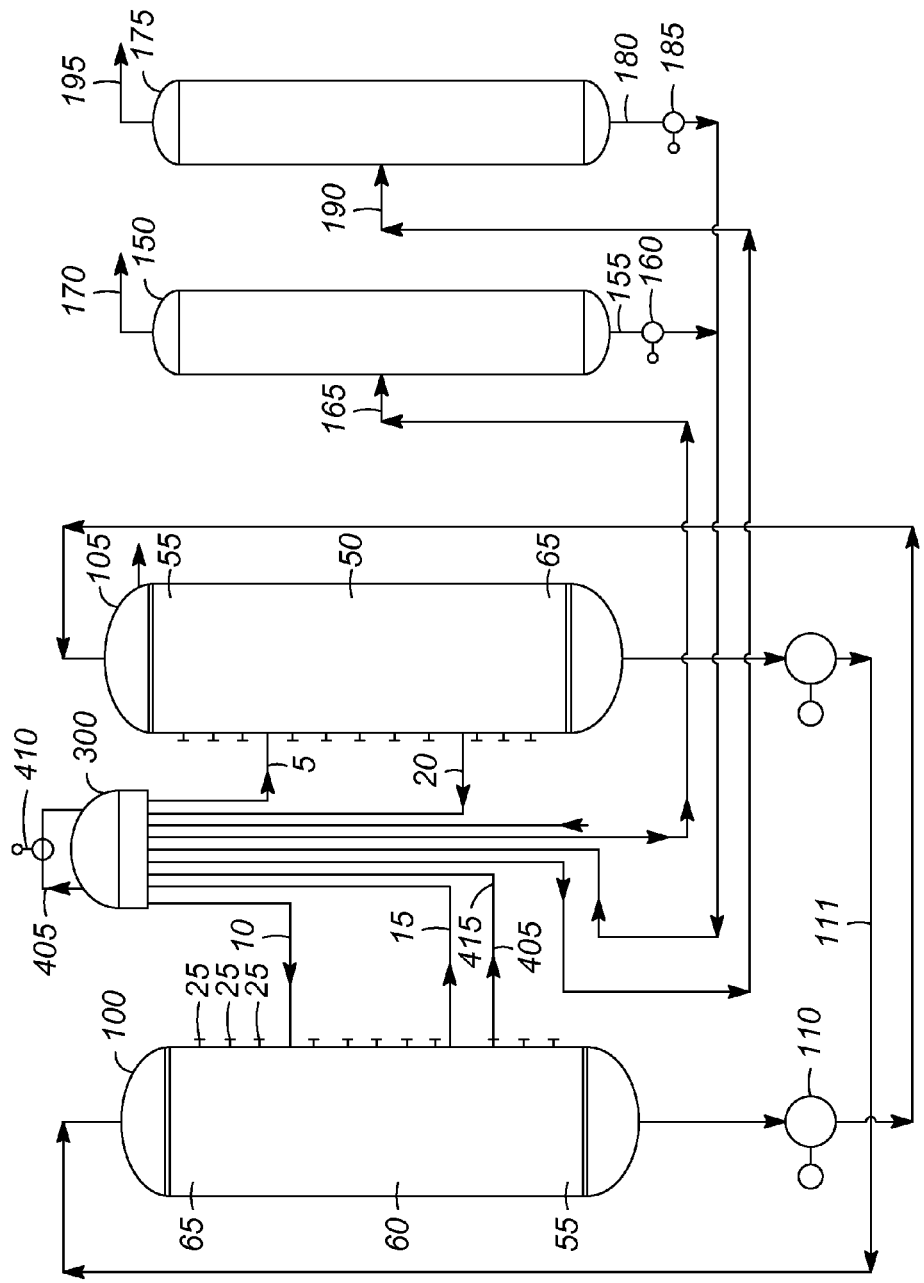
FIG. 4 is a simplified diagram of a simulated-moving-bed adsorption process in accordance with various embodiments of the invention.

Turning to FIG. 4, according to another aspect an adsorptive separation process includes a primary flush out 405 for flushing residual fluid in an intermediate transfer line of the purification zone 55, between the transfer line occupied by the feed stream 5 and the transfer line occupied by the extract stream 15 away from the adsorptive separation chamber 100 and 105 to remove at least a portion of the residual fluid from the intermediate transfer line. The process according to this aspect further includes directing the residual fluid flushed from the intermediate transfer line to another transfer line that is not a transfer line of the purification zone 55 to restrict the residual fluid from being introduced into the purification zone 55. In this manner, the residual fluid in the intermediate transfer line is not injected back into the purification zone as with previous systems, where components of the residual fluid would be separated, but without the benefit of flowing through the entire purification zone 55 prior to withdrawal via the extract stream 15 at the top of the purification zone 55.

In one aspect, the residual fluid flushed by the primary flush out 405 is transferred to and combined with the feed stream 5 to be introduced into the adsorptive separation chamber 105 with the feed stream 5 via the feed stream transfer line. In this manner, components of the residual fluid introduced with the feed stream may be separated within adsorptive separation unit with the feed fluid introduced via the feed stream 5. This provides more complete component separation than if the residual fluid were introduced directly into the purification zone 55 through an intermediate transfer line, because components in the residual fluid may flow through the entire purification zone 55 between the feed stream 5 and the extract stream 15 prior to being withdrawn via the extract stream 15. This approach may increase the purity of the extract stream 15 due to the more complete separation of the components of the residual fluid.

The residual fluid remaining in the intermediate transfer line that is flushed via the primary flush out 405 according to one approach may include residual feed fluid. To this end, the intermediate transfer line may have previously been occupied by the feed stream 5, so that the intermediate transfer line includes the residual feed fluid when the feed stream is shifted away therefrom at the end of a step. The residual feed fluid may advantageously be combined with the feed stream 5 and injected into the purification zone via the feed stream transfer line and port so components in the residual feed fluid are separated to about the same extent as the components of the feed stream 5 itself.

Because the pressure in the primary flush out 405 transfer line may be lower than the pressure in the feed stream transfer line, the primary flush fluid may need to be pumped in order to overcome the pressure differential and be combined with the feed stream 5. In this regard, a pump 410 may be provided for pumping the primary flush fluid through the intermediate transfer line and combining it with the feed stream 405. In one approach, the system may include a rotary valve, with the primary flush being flushed through the intermediate transfer line and to the rotary valve 300 where it is combined with the feed stream 5. However, at certain transfer lines or ports 25 along the adsorptive separation chambers 100 and 105 where two or more adsorptive separation chamber 100 and 105 are used, the pressure at the feed stream 5 may be higher than the pressure of the primary flush out stream 405 where the primary flush out stream 405 is transferred between a transfer line near the bottom of the adsorptive separation chambers 100 and 105 to join the feed stream 5 near the top of the other one of the adsorptive separation chambers 100 and 105. In these positions, residual feed in the line may surge into the extract stream because adjacent transfer lines are often in fluid communication with each other in processes utilizing a rotary valve 300. Thus, in one approach the pump 410 is positioned downstream of the rotary valve as illustrated in FIG. 4 to restrict the residual feed in the intermediate transfer line from back-flushing into the extract stream 15 when the streams are located at certain positions along the adsorptive separation chambers 100 and 105.

According to one aspect, the primary flush out 405 includes withdrawing fluid from the purification zone 55 of the adsorptive separation chamber 100 through a port 25 of the transfer line 415. The purification zone fluid is withdrawn from a location in the purification zone 55 adjacent to the port 25 and transferred into the intermediate transfer line in order to flush the residual fluid in the intermediate transfer line away from the adsorptive separation chamber 100. Flushing the intermediate transfer line 415 with purification zone fluid advantageously fills the transfer line 415 with fluid that is higher in concentration of the preferentially adsorbed component than the non-preferentially adsorbed component to reduce contamination of the extract stream 15 when the extract stream 15 arrives at the intermediate transfer line 415 in a subsequent step. In one approach, the purification zone material is withdrawn into the transfer line at a location near the transfer line currently occupied by the extract stream 15 so that the fluid within the purification zone 55 that is being withdrawn is similar in composition to the extract stream fluid. In one approach, the purification zone fluid is withdrawn through a port 25 and into a transfer line within two transfer lines from the transfer line currently occupied by the extract stream 15. In another approach, the purification zone fluid is withdrawn through a port 25 and into an intermediate transfer line of the purification zone 55 adjacent to the transfer line currently occupied by the extract stream 15. In this manner, the composition of the purification zone fluid used to flush the intermediate transfer line that will remain in the transfer line after the primary flush out will be similar in composition to the extract stream fluid and include only a small amount if any of the non-preferentially adsorbed components from the feed stream which would otherwise contaminate the extract stream 15 when it arrives at the intermediate transfer line during a subsequent step. In one example, the purification zone fluid withdrawn from the adsorptive separation chamber includes less than about 0.5% of the non-preferentially adsorbed component. In another example, the purification zone material used for the primary flush out 405 includes less than about 0.005% of the non-preferentially adsorbed component. As will be readily understood, according to this aspect, by transferring the primary flush out 405 and combining it with the feed stream 5, one less transfer line may be required when compared to a system that transfers the residual fluid from the primary flush out to another intermediate transfer line.

Figure 5:
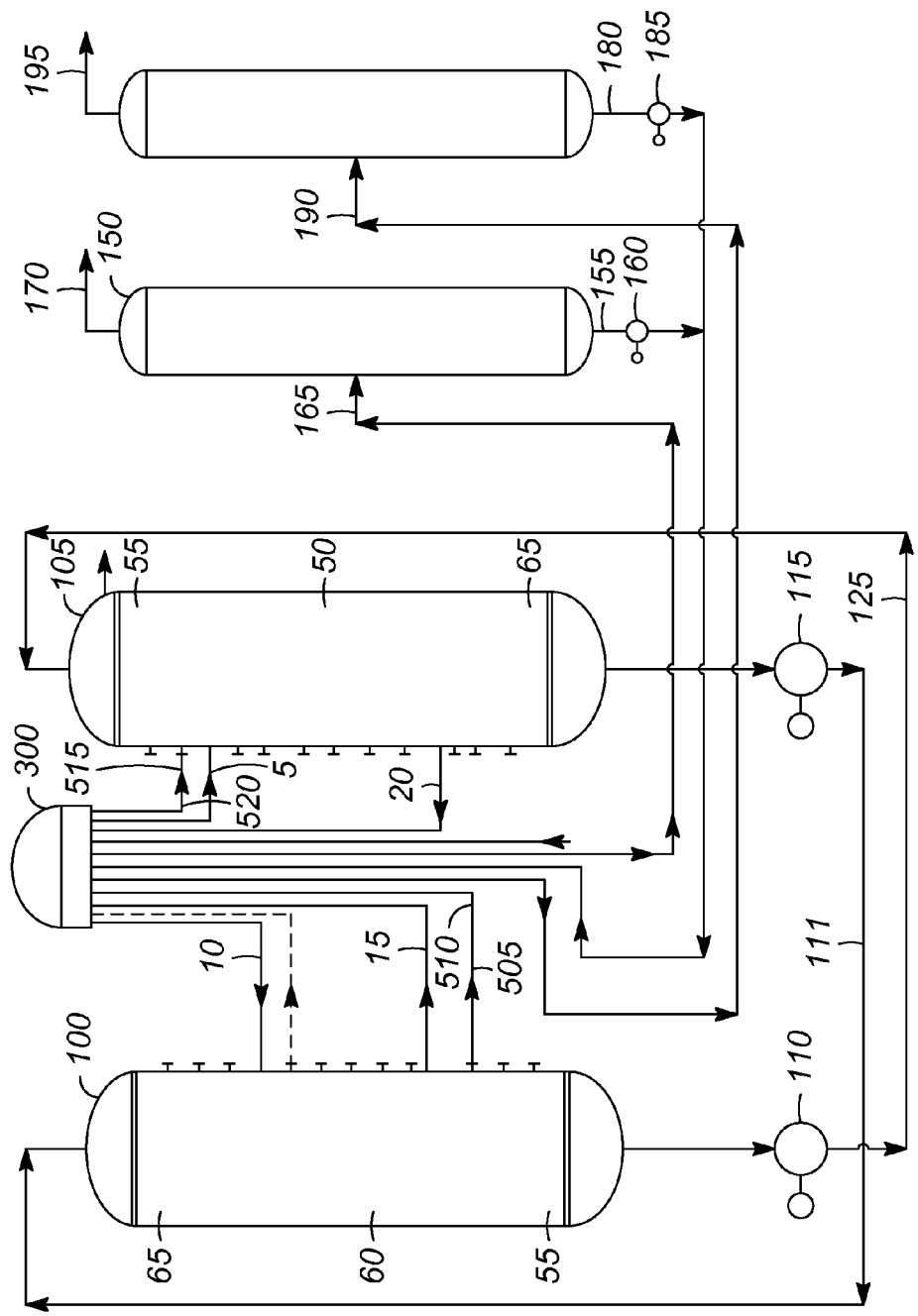
FIG. 5 is a simplified diagram of a simulated-moving-bed adsorption process in accordance with various embodiments of the invention.

A process and system for adsorptive separation of components from a feed stream according to another aspect is illustrated in FIG. 5. The process according to this aspect may include a primary flush out 505 similar to that described above in regard to FIG. 4. In contrast to the primary flush out 405 described above, however, the primary flush out 505 according to this aspect is directed to another transfer line of the purification zone 55 rather than combined with the feed stream 5. More particularly, the process includes flushing residual fluid within an intermediate transfer line 510 of the purification zone 55 between the feed stream 5 transfer line and the extract stream 15 transfer line away from the adsorptive separation chamber 100 or 105 to remove at least a portion of the residual fluid from the intermediate transfer line 510 via a primary flush out 505. The process further includes directing the residual fluid flushed from the intermediate transfer line 510 to another intermediate transfer line 515 of the purification zone 55 to flush residual fluid in the other intermediate transfer line 515 into the purification zone adjacent to the other intermediate transfer line 515 via a primary flush in 520.

According to one aspect, the other intermediate transfer line 515 includes residual feed fluid remaining in the intermediate transfer line 515 from the feed line 5 that occupied the intermediate transfer line 515 during a previous step. Thus, when flushing fluid is introduced into the intermediate transfer line 515 during the primary flush in 520, the residual feed fluid is introduced into the purification zone 55 of the adsorptive separation chamber 100 or 105. However, because the feed stream has already been shifted downstream of the primary flush in transfer line 515, the residual feed is introduced in an intermediate location of the purification zone. Thus, in one approach, in order to increase the amount of separation of components that occurs in the residual feed material in the purification zone 55, the primary flush in transfer line 515 is positioned between the primary flush out transfer line 510 and the transfer line currently occupied by the feed stream 5, so that the residual feed fluid is introduced into a portion of the purification zone near the feed stream. In one example, the primary flush in transfer line 515 is positioned within two transfer lines of the feed stream transfer line and in another example within one transfer line of the feed stream transfer line to increase the amount of separation of the components of the residual feed fluid that occurs in the purification zone 55.

The description above regarding the primary flush out 405 in regard to FIG. 4 also applies to the primary flush out 505 according to the aspect illustrated in FIG. 5 except that because the residual fluid in the intermediate transfer line is transferred to the transfer line 515 for the primary flush in 520, the intermediate transfer line 510 will not include primarily feed fluid when the primary flush out begins as was the case with primary flush out 405 described above. In this regard, residual fluid within the intermediate transfer line 510 will instead include fluid previously flushed from the primary flush out transfer line 510 to the primary flush in transfer line 515 during a previous step and thus will include primarily purification zone fluid withdrawn from the purification zone 55 as described above with regard to primary flush out 405.

Figure 6:
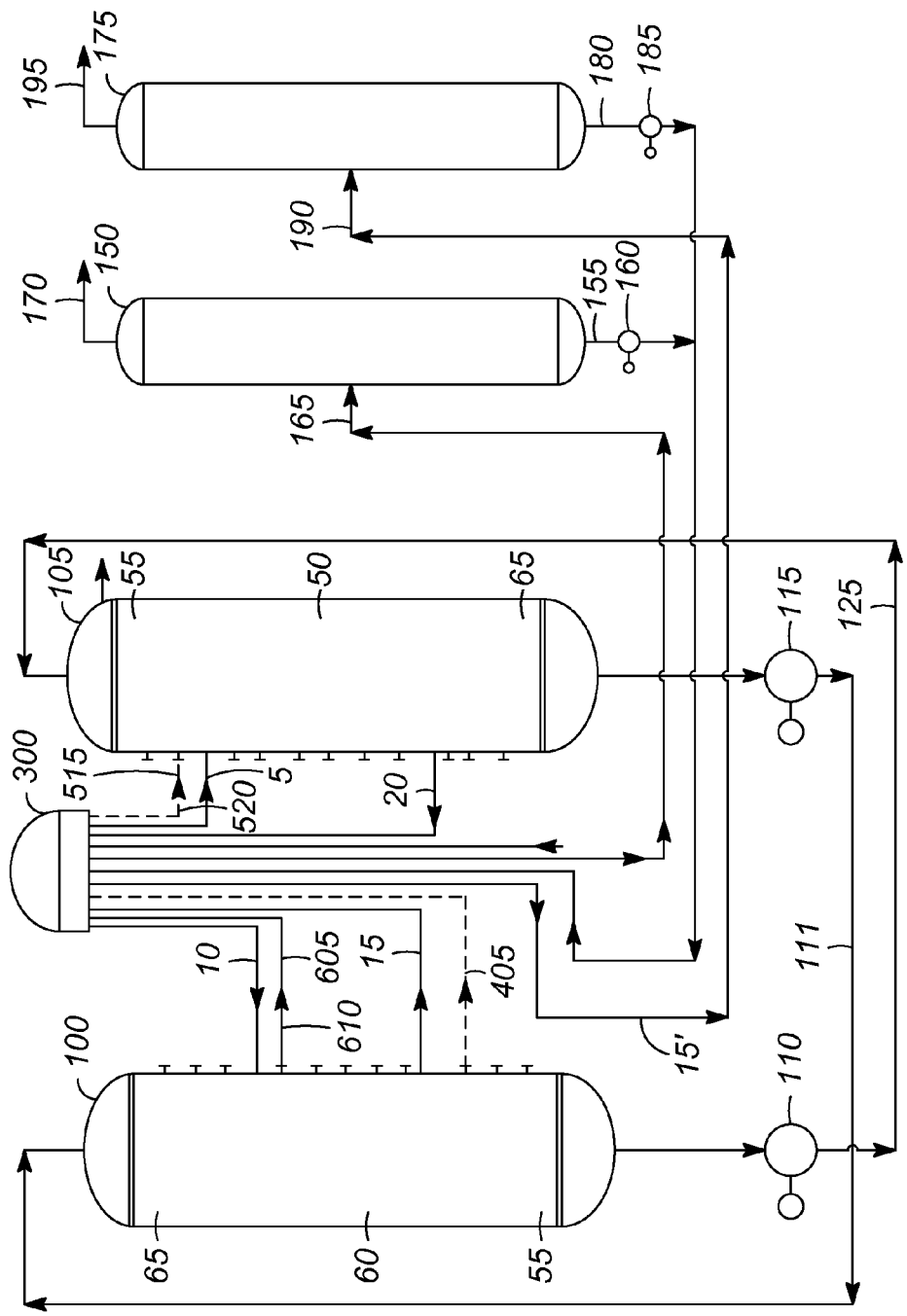
FIG. 6 is a simplified diagram of a simulated-moving-bed adsorption process in accordance with various embodiments of the invention.

Turning to FIG. 6, a process for adsorptive separation of components of a feed stream in accordance with another aspect is shown. According to this aspect, as described previously, an extract stream 15 is withdrawn from the adsorptive separation chamber 100. The extract stream 15 may be transferred to an extract separation device, e.g. the extraction fractionation column 175 for separation of the preferentially adsorbed component from the extract stream 15. The extract stream 15 may be directed to the extract fractionation column inlet 190 via an extract stream removal line 15'.

The process according to this aspect includes flushing an intermediate transfer line 610 of a desorption zone 60 between the extract stream 15 transfer line and the desorbent stream 10 transfer line away from the adsorptive separation chamber 100 via a secondary flush 605 to remove residual fluid from the intermediate transfer line 610. The process further includes directing the residual fluid flushed from the intermediate transfer line 610 to a downstream separation apparatus to separate components of the residual fluid. According to one aspect, since the intermediate transfer line 610 was previously occupied by the extract stream 15, the residual fluid in the intermediate transfer line 610 includes primarily extract fluid when the secondary flush 605 begins. In this regard, the residual extract fluid can be directed to the downstream separation apparatus to separate the preferentially adsorbed component from the extract fluid to increase the yield of the preferentially adsorbed component.

According to one aspect, the residual extract fluid flushed from the intermediate transfer line 610 is directed to the extract fractionation column inlet 175 so that the preferentially adsorbed component can be separated from the residual extract fluid via distillation to increase the yield of the extract product 195.

By one aspect, the secondary flush 605 includes flushing the residual fluid in the intermediate transfer line 610 with desorption zone flushing fluid withdrawn from the desorption zone 60 of the adsorptive separation chamber 100 via a corresponding port of the intermediate transfer line 610. In one example, intermediate transfer line 610 is within two transfer lines of the transfer line currently occupied by the desorbent stream 10 and in another example is within one transfer line of the transfer line currently occupied by the desorbent stream 10 so that the desorption zone flushing fluid is similar in composition to the desorbent stream 10. In this manner, the desorption zone flushing fluid remains in the intermediate transfer line 610 after the secondary flush 605 has occurred. Upon shifting of the desorbent stream to the intermediate transfer line 610 in a subsequent step the residual desorption zone fluid remaining in the intermediate transfer line 610 is introduced into the adsorptive separation chamber 100 with the desorbent stream so that the desorbent zone fluid is similar in composition to the desorbent stream 10.

In accordance with another aspect, a process is provided for adsorptive separation of components of a feed stream that includes flushing an intermediate transfer line located between two of the feed stream 5, extract stream 15, desorbent stream 10, and raffinate stream 20 to remove residual fluid from the intermediate transfer line. The process, according to this aspect includes generally flushing the intermediate transfer line at a dynamic or non-constant volumetric flow rate during at least two different portions of a step-time interval.

As described previously, in accordance with various aspects of the invention, countercurrent adsorptive separation includes introducing a feed stream 5, comprising at least one preferentially adsorbed component and at least one non-preferentially adsorbed component, and a desorbent stream 10 into two different ports 25 via two different corresponding transfer lines along a multi-bed adsorptive separation chamber having a plurality of beds that are serially connected in fluid communication and comprising a predetermined number of spaced ports with corresponding transfer lines in fluid communication therewith for introducing and removing fluid into and from the adsorptive separation chamber and withdrawing an extract stream 15 and raffinate stream 20 through two different ports of the multi-bed adsorptive separation chamber via two different corresponding transfer lines. The various streams that are introduced and withdrawn to and from the adsorptive separation chamber 100 and 105 are sequentially shifted or stepped downstream to subsequent ports. The various streams are typically stepped simultaneously to subsequent ports 25, for example by rotating a rotary valve 300, and are maintained at a particular port 25 or step for a predetermined step-time interval. As discussed above, in one approach, there are between about 4 and 100 ports 25, between about 12 and 48 ports in another approach, and between about 20 and 30 ports in yet another approach, and an equal number of corresponding transfer lines. In one example, the adsorptive separation chamber or chambers 100 and 105 include about 24 ports and each stream is shifted to each of the 24 ports 25 during a complete cycle so that each stream occupies each port 25 and corresponding transfer line during the cycle. In this example, a cycle may be between about 20 and about 40 minutes in one approach and between about 22 and 35 minutes in another approach. In one approach, a step-time interval is between about 30 seconds and about two minutes. In another approach, the step-time interval is between about 45 seconds and about one minute thirty seconds. In yet another approach, the step-time interval is between about 50 seconds and about one minute and 15 seconds.

In this regard, the process includes flushing an intermediate transfer line between two lines currently occupied by two of the typical streams, including the feed stream 5, the desorbent stream 10, the extract stream 15, and the raffinate stream 20 at a non-uniform or dynamic volumetric flow rate during the step-time interval. According to one aspect the process includes flushing the intermediate transfer line at a first flow rate for a first portion of the step-time interval. The process includes flushing the intermediate transfer line at a second flow rate for a second portion of the step-time interval later during the step-time interval than the first portion. In this manner, a greater volume of fluid is flushed from the intermediate transfer line during one of the first and second portion of the step-time interval than during the other portion. Flushing the transfer line at a non-constant flow rate may provide performance advantages in terms of the composition of fluid flushed into or from the intermediate transfer line as well as the timing of introducing fluids to or from the intermediate transfer line.

Figure 10:
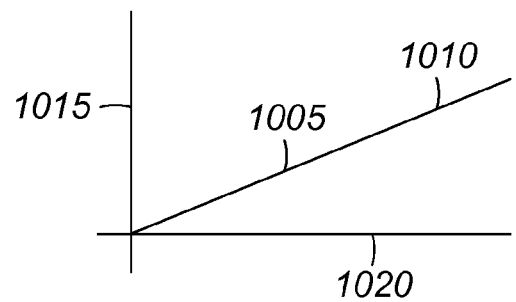
FIGS. 10-12 are graphs illustrating the volumetric flow rate of fluid through transfer lines in accordance with various embodiments of the invention.
Figure 11:
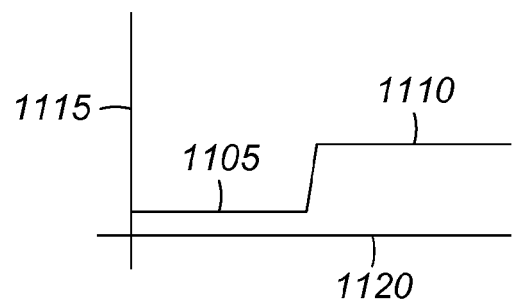
Figure 12:
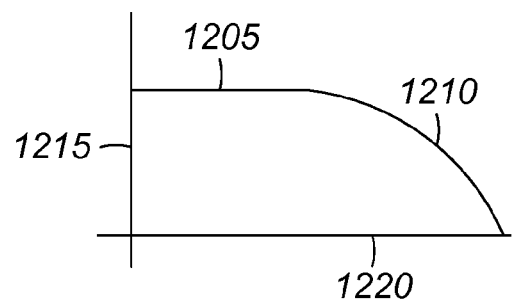

In one aspect, the non-constant flow rate may include a ramped or exponentially increasing or decreasing flow rate that increases or decreases during at least a portion of the step-time interval. In this regard, the ramped flow rate may increase or decrease during a portion of the step-time interval and may vary linearly or non-linearly, e.g. exponentially during that time. By another aspect, the non-constant flow rate may include step increases or decreases in the flow rate so that one or both of the first flow rate and the second flow rate is constant and one is different than the other of the first flow rate and the second flow rate. In yet another aspect, the non-constant flow rate may include a combination of ramped portions and step increases and decreases in the volumetric flow rate. The non-constant flow rate may also include additional flow rates during additional portions of the step-time interval. The flow rate may increase, decrease, or remain unchanged during any particular step. In addition the flow rate may be changed from the initial value to a higher value, lower value or zero at the conclusion of a step. FIGS. 10-12 illustrate examples of non-constant flow rates in accordance with various aspects of the invention. FIG. 10 illustrates a ramped flow rate 1015 that increases over time 1020 during at least a portion of the step-time interval. In this example, a first flow rate 1005 is lower than a second flow rate 1010 so that a greater volume of fluid is flushed during the second portion of the step-time interval than during the first portion. In another example, the ramped flow rate decreases over time so that a first flow rate is higher than a second flow rate so that a greater volume of fluid is flushed during the first portion of the step-time interval than during the second portion. FIG. 11 on the other hand illustrates an example of a non-constant stepped flow rate. In this example, the flow rate 1115 is at a first generally constant flow rate 1105 during a first portion of the step-time interval 1120 and increases to a second and generally constant higher flow rate 1110 during the second portion of the step-time interval 1120. In another example, the stepped flow rate has a second generally constant flow rate during the second portion of the step-time interval that is lower than a first flow rate so that so that more volume of fluid is flushed during the first potion of the step-time interval. The volumetric flow rate during one of the first and second portions may be zero according to various aspects. In yet another example, illustrated in FIG. 12, the flow rate 1215 at a first portion of the step-time interval 1220 begins at a first flow rate 1205 and then includes second flow rate 1210 that exponentially decreases over time during a second portion of the step-time interval 1220. Other flow rate profiles are also contemplated in accordance with various aspects of the invention that have different first and second flow rates during corresponding first and second portions of the step-time interval and may there may be additional portions of the step-time interval with still other flow rates.

In accordance with one aspect, one of the first and second flow rates is sufficient to flush between about 50% and 400% of the volume of the transfer line being flushed and associated valving so that most or all of the residual fluid within the transfer line is flushed during the first or second portion of the step-time interval. According to another aspect, one of the first and second flow rates is sufficient to flush between about 75% and about 200% of the transfer line and associated valving volume during the first or second portion of the step-time interval. In yet another aspect, one of the first and second flow rates is sufficient to flush between about 90% and about 150% of the transfer line and associated valving volume during the first or second portion of the step-time interval. The other of the first and second flow rates according to various aspects may be sufficient to flush between about 0% and about 75% of the transfer line and valving volume in one approach, between about 0% and about 50% of the transfer line and valving volume in another approach, and between about 0% and about 25% of the transfer line valving volume in yet another approach.

According to one aspect, the first flow rate is higher than the second flow rate so that a greater volume of fluid is flushed during the first portion of the step-time interval than during the second portion of the step-time interval. The process according to this aspect may be particularly beneficial when the process includes flushing residual fluid in the intermediate transfer line into the adsorptive separation chamber 100 and 105 so that the residual fluid has a greater dwell time within the chamber 100 and 105 before being subsequently withdrawn than it otherwise would if the flow rate was constant during the step-time interval or if the second flow rate was greater than the first flow rate.

According to another aspect, the second flow rate is higher than the first flow rate so that a greater volume of fluid is flushed during the second portion of the step-time interval than during the first portion of the step-time interval. The process according to this aspect may be particularly useful where residual fluid is being flushed away from the adsorptive separation chamber 100 and 105 with flushing fluid withdrawn from the adsorptive separation chamber 100 and 105. In this regard, the flushing fluid is provided a greater dwell time within the adsorptive separation chamber than when a constant flow rate is used or when the first flow rate is greater than the second flow rate. This advantageously provides for greater separation of components in the flushing fluid so that the flushing fluid will be more similar in composition than a subsequent stream withdrawn from or introduced into the adsorptive separation chamber 100 and 105.

Figure 7:
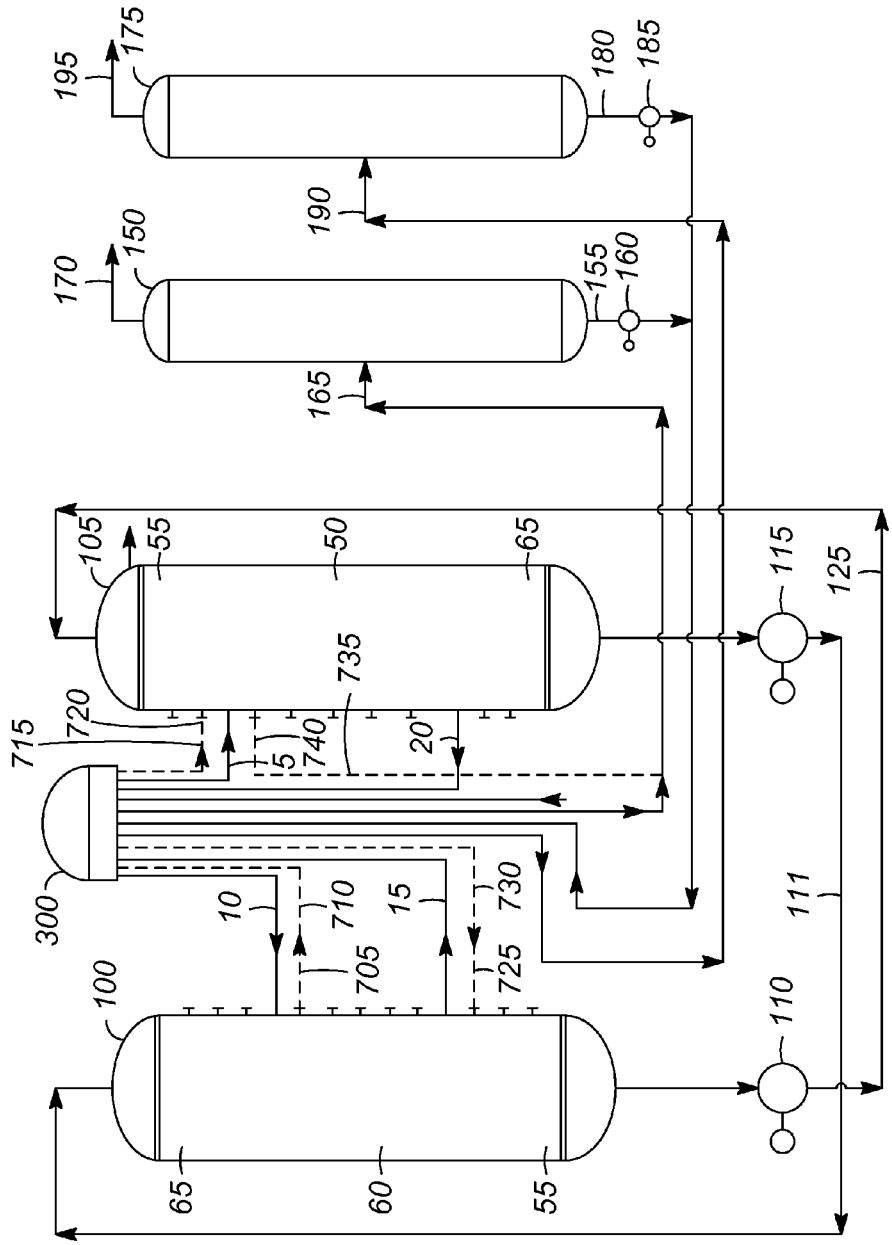
FIG. 7 is a simplified diagram of a simulated-moving-bed adsorption process in accordance with various embodiments of the invention.

Turning to more of the particulars, the following examples generally include a process wherein a feed stream 5 and a desorbent stream 10 are introduced into different ports 25 via different transfer lines of the adsorptive separation chamber 100 and 105. An extract stream 15 and a raffinate stream 20 are withdrawn through two other ports 25 via two different transfer lines of the adsorptive separation chamber 100 and 105. According to one aspect, as illustrated for example in FIG. 7, a primary flush in 720 includes flushing an intermediate transfer line 715 between a transfer line currently occupied by the feed stream 5 during a step and a transfer line occupied by the extract stream 15 during the step. The residual fluid in the transfer line 715 may include primarily residual feed fluid. The process according to this aspect includes flushing the transfer line 715 at a higher first volumetric flow rate during the first portion of the step-time interval than a second volumetric flow rate during the second portion of the step-time interval. In this manner, a greater volume of the residual feed fluid is flushed into the adsorptive separation chamber 100 or 105 during the initial first portion of the step-time interval than during the subsequent second portion. In this regard, the residual feed fluid flushed into the adsorptive separation chamber 100 or 105 is provided greater dwell time in the adsorptive separation chamber 100 and 105 and access to the adsorbent therein for separation of the non-preferentially adsorbed component prior to withdrawal thereof through the extract stream 15 in a subsequent step. According to another aspect, the process includes a primary flush out 710 which includes flushing an intermediate transfer line 705 away from the adsorptive separation chamber 100 or 105 with fluid withdrawn from the chamber as described previously. In one example, the process includes flushing the transfer line 705, which may include residual extract fluid from being previously occupied by the extract stream, at a first volumetric flow rate during a first portion of the step-time interval that is less than a second volumetric flow rate during a second subsequent portion of the step-time interval. In this manner, the flushing fluid withdrawn from the desorption zone 60 may include fluid similar in composition to the desorbent stream 10. The process may include flushing the residual extract fluid from the intermediate transfer line 705 to the intermediate transfer line 715 to flush the residual feed fluid in the intermediate extract stream 715 into the purification zone 55. In one approach, the process includes flushing the fluid at a first flow rate at the first portion of the step-time interval that is greater than the second flow rate during the second portion of the step-time interval so that a greater volume of the residual feed fluid is introduced into the purification zone 55 during an earlier portion of the step-time interval so that more separation of the feed fluid can be achieved in the purification zone 55 prior to the extract stream 15 subsequently arriving at and being withdrawn through the intermediate transfer line 715 to increase the purity of the extract stream.

Similarly, with reference briefly to FIG. 6 as described previously, the process may instead include a secondary flush 605 that includes flushing the intermediate transfer line 610 and directing the residual fluid flushed therefrom to a downstream separation apparatus, including in one example, an extract separation column 175 to separate the preferentially adsorbed component from the residual extract fluid in the intermediate transfer line 610. The process according to this aspect may include flushing the intermediate transfer line 610 at a first volumetric flow rate during a first portion of the step-time interval that is less than a second volumetric flow rate during a second subsequent portion of the step-time interval. In this manner, the flushing fluid withdrawn from the desorption zone 60 may include fluid similar in composition to the desorbent stream 10.

According to another aspect, an intermediate transfer line 725 may be flushed with flushing fluid to introduce residual fluid in the intermediate transfer line into the purification zone 55. In accordance with this aspect, the process may include flushing the intermediate transfer line 725 at a first flow rate during a first portion of the step-time interval that is greater than a second flow rate during a subsequent second portion of the step-time interval so that a greater volume of the residual fluid in the transfer line 725 is flushed into the purification zone 55 during the first portion of the step-time interval than during the second portion. In this manner, the residual fluid will be present in the purification zone for a longer dwell time for separation of components therein prior to being withdrawn by the extract stream 15 when arrives at the intermediate transfer line 725 in a subsequent step.

In another aspect, an intermediate transfer line 735 may be flushed with a flushing fluid away from the adsorptive separation chamber 100 or 105 to remove residual fluid therefrom. In one approach, the intermediate transfer line includes residual raffinate from the raffinate stream 20 that occupied the intermediate transfer line 735 during a previous step of the cycle. In accordance with this aspect, the process includes flushing the intermediate transfer line 735 with flushing fluid withdrawn from the adsorption zone 50 at a first flow rate during a first portion of the step-time interval that is less than a second portion of the step-time interval. In this manner, the flushing fluid will be present in the adsorptive separation chamber 100 or 105 for a greater amount of time prior to being withdrawn through the intermediate transfer line for flushing the residual feed fluid therefrom. Accordingly, the flushing fluid from the adsorption zone 55 will have a similar composition to the feed stream and will include less of the non-preferentially adsorbed component of the raffinate stream. After flushing the intermediate transfer line, the flushing fluid will remain therein as residual fluid that will be introduced with the feed stream 5 when the feed stream 5 is introduced through the intermediate transfer line 735 during a subsequent step to reduce contamination of the feed stream by an excess of non-preferentially adsorbed component.

Turning to FIGS. 1, 4, and 5, according to various aspects as described previously, the intermediate transfer lines 45, 415, or 510 may be flushed away from the adsorptive separation chamber 100 or 105 to remove residual fluid therefrom. The intermediate transfer lines 45, 415, or 510 may be flushed by withdrawing flushing fluid from the purification zone 55 into the intermediate transfer line to displace the residual fluid away from the adsorptive separation chamber 100 or 105 and will subsequently be filled with residual flushing fluid from the purification zone 55. According to one aspect, the process includes flushing the intermediate transfer line 45, 415, or 510 at a first flow rate during a first portion of the step-time interval and at a second flow rate that is greater than the first flow rate during a subsequent second portion of the step-time interval. In this manner, the flushing fluid is provided with additional time in the purification zone 55 and access to the adsorbent therein for separation of the non-preferentially adsorbed component so that when the purification zone fluid is withdrawn for flushing the intermediate transfer line 45, 415, or 510, it will be similar in composition to the extract stream 15 that will be withdrawn therethrough during a subsequent step. The process according to this aspect advantageously reduces the amount of the non-preferentially adsorbed component that remains in residual fluid within the intermediate transfer line 45, 405, or 510 that would otherwise contaminate the extract stream 15 during withdrawal therethrough, thereby increasing the purity of the extract stream 15. In one approach, as described previously, the intermediate transfer line 415 is in communication with the feed stream transfer line so that the residual fluid flushed from the intermediate transfer line is combined with the feed stream 5. In another approach, as described above, the intermediate transfer line 510 is in communication with another intermediate transfer line 515 so that the residual fluid therein is flushed to the other intermediate transfer line 515 to flush residual feed fluid therein into a downstream portion of the purification zone 55.

In accordance with various aspects, the volumetric flow rate of the fluid through the transfer lines during dynamic flushing thereof may be controlled using valving and a controller. The valving may be incorporated into transfer lines themselves to control or restrict the volumetric flow rate of fluid flowing therethrough. A controller may be provided for controlling the valves and the flow rate of the fluid through the transfer lines. The valving may also be incorporated in other locations within the system, for example on the downstream side of a rotary valve 300 when a rotary valve is incorporated or in downstream lines for transferring the fluid to downstream components of the system, for example the lines 15' and 20' for transferring fluid to the extract fractionation column 175 or the raffinate fractionation column 150, respectively.

In selecting an adsorbent for the present simulated-moving-bed process, the only limitation is the effectiveness of the particular adsorbent/desorbent combination in the desired separation. An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process.

The practice of the subject invention thus is not related to or limited to the use of any particular adsorbent or adsorbent/desorbent combination, as differing sieve/desorbent combinations are used for different separations. The adsorbent may or may not be a zeolite. Examples of adsorbents which may be used in the process of this invention include nonzeolitic molecular sieves including carbon-based molecular sieves, silicalite and the crystalline aluminosilicates molecular sieves classified as X and Y zeolites. Details on the composition and synthesis of many of these microporous molecular sieves are provided in U.S. Pat. No. 4,793,984, which is incorporated herein for this teaching. Information on adsorbents may also be obtained from U.S. Pat. Nos. 4,385,994; 4,605,492; 4,310,440; and 4,440,871.

In adsorptive separation processes, which generally are operated continuously at substantially constant pressures and temperatures to insure liquid phase, the desorbent material must be selected to satisfy several criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost. The desorbent may include a heavy or light desorbent depending on the particular application. The terms heavy and light are in reference to the boiling point of the desorbent relative to the C8 aromatics, namely, ortho-, meta-, para-xylene and ethylbenzene. Those skilled in the art will appreciate that the designator "C8" refers to a compound comprising eight (8) carbon atoms. In certain embodiments, the heavy desorbent is selected from the group consisting of para-diethylbenzene, para-diisopropylbenzene, tetralin, and the like, and combinations thereof. In certain embodiments, toluene and the like can be used as the light desorbent. The para-diethylbenzene (p-DEB) has a higher boiling point than the C8 aromatic isomers and, as such, the p-DEB is the bottoms (i.e., heavy) product when separated from the C8 isomers in a fractional distillation column. Similarly, toluene has a lower boiling point than the C8 aromatic isomers and, as such, the toluene is the overhead (i.e., light) product when separated from the C8 isomers in a fractional distillation column. The p-DEB has become a commercial standard for use as a desorbent in separations of para-xylene.

Adsorption conditions in general include a temperature range of from about 20° to about 250° C., with from about 60° to about 200° C. being preferred for para-xylene separation. Adsorption conditions also include a pressure sufficient to maintain liquid phase, which may be from about atmospheric to 2 MPa. Desorption conditions generally include the same range of temperatures and pressure as used for adsorption conditions. Different conditions may be preferred for other extract compounds.

The above description and examples are intended to be illustrative of the invention without limiting its scope. While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

The invention claimed is:

1. A process for separating components in a feed stream by simulated countercurrent adsorptive separation comprising:
introducing a feed stream, comprising at least one preferentially adsorbed component and at least one non-preferentially adsorbed component, and a desorbent stream into two different ports via two different corresponding transfer lines along a multi-bed adsorptive separation chamber having a plurality of beds that are serially connected in fluid communication and comprising a predetermined number of spaced ports with corresponding transfer lines in fluid communication therewith for introducing and removing fluid into and from the adsorptive separation chamber and withdrawing an extract stream and raffinate stream through two different ports of the multi-bed adsorptive separation chamber via two different corresponding transfer lines;
flushing an intermediate transfer line between the feed stream transfer line and the extract stream transfer line away from the adsorptive separation chamber to remove residual fluid from the intermediate transfer line; and directing the residual fluid flushed from the intermediate transfer line to a recycle stream to introduce the residual fluid into the adsorptive separation chamber.

2. The process of claim 1, further comprising flushing another intermediate transfer line between the feed stream transfer line and the intermediate transfer line with a flushing fluid comprising the preferentially adsorbed component in a concentration higher than the concentration in the feed stream and the non-preferentially adsorbed component in a concentration lower than in the feed stream to displace residual feed from the intermediate transfer line so that the flushing fluid becomes the residual fluid in the intermediate transfer line when the intermediate transfer line is subsequently flushed.

3. The process of claim 2, wherein the flushing fluid is withdrawn from a transfer line previously occupied by an extract withdrawal stream, adjacent to a desorption zone defined as a region of the adsorptive separation chamber between the port where the desorbent stream is introduced into the adsorptive separation chamber and the port where the extract stream is withdrawn from the adsorptive separation chamber and sent to the other intermediate transfer line to flush the residual feed therefrom.

4. The process of claim 1, wherein the feed stream, the desorbent stream, the extract stream, the raffinate stream, and the intermediate flush are sequentially shifted to subsequent ports and their corresponding transfer lines along the predetermined number of spaced ports and their corresponding transfer lines and the extract stream is withdrawn by a transfer line previously flushed by intermediate flush to reduce contamination of the extract stream with the non-preferentially adsorbed component remaining in residual fluid in the transfer line.

5. The process of claim 1, wherein flushing the intermediate transfer line includes withdrawing fluid from a purification zone of the adsorptive separation chamber defined as a region of the adsorptive separation chamber between the port into which the feed is introduced and the port from which the extract is withdrawn and displacing the residual fluid in the transfer line with the purification zone fluid.

6. The process of claim 5, wherein flushing the intermediate transfer line further includes flushing a transfer line within two transfer lines of the transfer line from which the extract stream is currently being withdrawn so that the purification zone fluid flushed into the intermediate flush transfer line is similar in composition to the extract stream.

7. The process of claim 1, wherein the residual fluid flushed from the intermediate transfer line is sent to a bottoms portion of a raffinate fractionation column to be sent to the recycle stream so that the residual fluid is not heated to a raffinate column bottoms outlet temperature to reduce energy consumption.

8. The process of claim 1, wherein the residual fluid flushed from the intermediate transfer line is sent to a bottoms portion of an extract fractionation column to be sent to the recycle stream so that the residual fluid is not heated to an extract column bottoms outlet temperature to reduce energy consumption.

9. The process of claim 1 wherein the feed stream comprises $C_8$ aromatics and the extract stream is separated downstream to form an extract product comprising high-purity meta-xylene.

10. The process of claim 1 wherein the feed stream comprises $C_8$ aromatics and the extract stream is separated downstream to form an extract product comprising high-purity para-xylene.

11. A process for the separation of components in a feed stream comprising at least one preferentially adsorbed component and at least one non-preferentially adsorbed component by simulated countercurrent adsorptive separation comprising sequentially:

introducing a feed stream into a port of a multi-bed adsorptive separation chamber comprising a plurality of ports with corresponding transfer lines via a transfer line in fluid communication with the port;

flushing residual feed from the transfer line into the adsorptive separation chamber with a flushing fluid to fill the transfer line with the flushing fluid;

flushing residual flushing fluid in the transfer line away from the adsorptive separation chamber with fluid from a purification zone of the adsorptive separation chamber adjacent to the port to fill the transfer line with the purification zone fluid; and withdrawing an extract stream from the adsorptive separation chamber through the transfer line.

12. The process of claim 11, wherein the extract stream is withdrawn through the transfer line along with residual purification zone fluid remaining within the transfer line from flushing the residual flushing fluid away from the adsorptive separation chamber.

13. The process of claim 12, further comprising transferring the extract stream and the residual purification zone fluid in the transfer line through an inlet of an extract fractionation column to separate the preferentially adsorbed component.

14. The process of claim 11, further comprising transferring the residual flushing fluid from the transfer line to a recycle stream to be returned to the adsorptive separation chamber.

15. The process of claim 11, further comprising transferring the residual flushing fluid from the transfer line to a bottoms portion of a raffinate fractionation column before it is transferred to the recycle stream so that it is not heated to a raffinate column bottoms outlet temperature to conserve energy.

16. The process of claim 11, further comprising transferring the residual flushing fluid from the transfer line to a bottoms portion of an extract fractionation column before it is transferred to the recycle stream so that it is not heated to an extract column bottoms outlet temperature to conserve energy.

17. The process of claim 11, wherein the flushing fluid comprises desorbent and the preferentially adsorbed component and less than a predetermined amount of the non-preferentially adsorbed component.

18. The process of claim 12, wherein the process is carried out sequentially at each of the ports and corresponding transfer lines along the multi-bed adsorptive separation chamber.

* * * * *